(12) United States Patent
Arnsten

(10) Patent No.: US 10,022,341 B2
(45) Date of Patent: Jul. 17, 2018

(54) METHODS OF PREVENTING NEURODEGENERATION OF ASSOCIATION CORTEX IN A MAMMAL

(71) Applicant: YALE UNIVERSITY, New Haven, CT (US)

(72) Inventor: Amy F. T. Arnsten, Bethany, CT (US)

(73) Assignee: Yale University, New Haven, CT (US)

( * ) Notice: Subject to any disclaimer, the term of this patent is extended or adjusted under 35 U.S.C. 154(b) by 0 days.

(21) Appl. No.: 15/532,420

(22) PCT Filed: Dec. 2, 2015

(86) PCT No.: PCT/US2015/063428
§ 371 (c)(1),
(2) Date: Jun. 1, 2017

(87) PCT Pub. No.: WO2016/089997
PCT Pub. Date: Jun. 9, 2016

(65) Prior Publication Data
US 2017/0360724 A1    Dec. 21, 2017

Related U.S. Application Data

(60) Provisional application No. 62/086,363, filed on Dec. 2, 2014.

(51) Int. Cl.
| | | |
|---|---|---|
| *A61K 31/165* | (2006.01) | |
| *A61K 31/54* | (2006.01) | |
| *A61K 31/498* | (2006.01) | |
| *A61K 31/4174* | (2006.01) | |
| *A61K 31/198* | (2006.01) | |
| *A61K 31/155* | (2006.01) | |
| *A61K 31/4168* | (2006.01) | |

(52) U.S. Cl.
CPC .......... *A61K 31/165* (2013.01); *A61K 31/155* (2013.01); *A61K 31/198* (2013.01); *A61K 31/4168* (2013.01); *A61K 31/4174* (2013.01); *A61K 31/498* (2013.01); *A61K 31/54* (2013.01)

(58) Field of Classification Search
None
See application file for complete search history.

(56) References Cited

U.S. PATENT DOCUMENTS

| | | | |
|---|---|---|---|
| 5,169,645 A | 12/1992 | Shukla et al. | |
| 2004/0116436 A1* | 6/2004 | Tatton ................. | A61K 31/498 514/249 |
| 2011/0065796 A1 | 3/2011 | Whomsley et al. | |
| 2012/0065152 A1 | 3/2012 | Whomsley et al. | |

FOREIGN PATENT DOCUMENTS

| | | |
|---|---|---|
| WO | 2007016284 A2 | 2/2007 |
| WO | 2011033296 A1 | 3/2011 |

OTHER PUBLICATIONS

International Search Report and Written Opinion for PCT International Application No. PCT/US2015/063428 dated Feb. 12, 2016.
Acin-Perez, et al., Protein phosphorylation and prevention of cytochrome oxidase inhibition by ATP: coupled mechanisms of energy metabolism regulation, Cell Metab. 13(6) ,2011 ,712-719.
Arnsten, et al.,Neuromodulation of thought: flexibilities and vulnerabilities in prefrontal cortical network synapses, Neuron. 76(1) ,2012 ,223-239.
Braak, et al.,Stages of the pathologic process in Alzheimer disease: age categories from 1 to 100 years, J Neuropathol Exp Neurol. 70(11) ,2011 ,960-969.
Bussiére, et al.,Progressive degeneration of nonphosphorylated neurofilament protein-enriched pyramidal neurons predicts cognitive impairment in Alzheimer's disease: stereologic analysis of prefrontal cortex area 9, J Comp Neurol. 463(3) ,2003 ,281-302.
Camandola, et al.,Aberrant subcellular neuronal calcium regulation in aging and Alzheimer's disease, Biochim Biophys Acta. May 2011;1813(5) ,2011 ,965-973.
Carlyle, et al.,cAMP-PKA phosphorylation of tau confers risk for degeneration in aging association cortex, Proc Natl Acad Sci U S A. 111(13) ,2014 ,5036-5041.
Chou, et al.,Quantitative analysis of dose-effect relationships: the combined effects of multiple drugs or enzyme inhibitors, Adv Enzyme Regul. 22 ,1984 ,27-55.
Ferreira, et al.,Multiple defects in energy metabolism in Alzheimer's disease, Curr Drug Targets. 11(10) ,2010 ,1193-1206.
Giannakopoulos, et al.,Tangle and neuron numbers, but not amyloid load, predict cognitive status in Alzheimer's disease, Neurology. 60(9) ,2003 ,1495-1500 (Abstract Only).
Holford, et al.,Understanding the dose-effect relationship: clinical application of pharmacokinetic-pharmacodynamic models, Clin Pharmacokinet. 6(6) ,1981 ,429-453.
Jicha, et al.,cAMP-dependent protein kinase phosphorylations on tau in Alzheimer's disease, J Neurosci. 19(17) ,1999 ,7486-7494.
Lewis, et al.,Laminar and regional distributions of neurofibrillary tangles and neuritic plaques in Alzheimer's disease: a quantitative study of visual and auditory cortices, J Neurosci. 7(6) , 1987 ,1799-1808.
Loewe, et al.,Effect of combinations: mathematical basis of the problem, Arch. Exp. Pathol. Pharmakol. 114 ,1926 ,313-326.
Mattson, et al.,ER calcium and Alzheimer's disease: in a state of flux, Sci Signal. 3(114):pe10 ,2010.
Paspalas, et al.,Constellation of HCN channels and cAMP regulating proteins in dendritic spines of the primate prefrontal cortex: potential substrate for working memory deficits in schizophrenia, Cereb Cortex. 23(7) ,2013 ,1643-1654.

(Continued)

*Primary Examiner* — Brian J Davis
(74) *Attorney, Agent, or Firm* — Saul Ewing Arnstein & Lehr LLP; Kathryn Doyle; Domingos J. Silva

(57) ABSTRACT

The present invention provides methods of preventing and/or reducing risk of neurodegeneration of association cortex, and/or inhibiting or reversing formation of phosphorylated tau or COXIV in the prefrontal cortex of a mammal in need thereof. In certain embodiments, the method comprises administering to the mammal a therapeutically effective amount of an $\alpha_{2A}$-adrenergic receptor agonist.

15 Claims, 22 Drawing Sheets

(56) References Cited

OTHER PUBLICATIONS

Pearson, et al.,Anatomical correlates of the distribution of the pathological changes in the neocortex in Alzheimer disease, Proc Natl Acad Sci U S A. 82(13) ,1985 ,4531-4534.
Pei, et al.,Role of protein kinase B in Alzheimer's neurofibrillary pathology, Acta Neuropathol. 105(4) ,2003 ,381-392.
Platt, et al.,Transgenic models of Alzheimer's disease: better utilization of existing models through viral transgenesis, Biochim Biophys Acta. 1832(9) ,2013 ,1437-1448.
Sadik, et al.,Phosphorylation of tau at Ser214 mediates its interaction with 14-3-3 protein: implications for the mechanism of tau aggregation, J Neurochem. 108(1) ,2009 ,33-43.
Sengupta, et al.,Phosphorylation of tau at both Thr 231 and Ser 262 is required for maximal inhibition of its binding to microtubules, Arch Biochem Biophys. 357(2) ,1998 ,299-309.

* cited by examiner

Fig. 2A
Fig. 2B
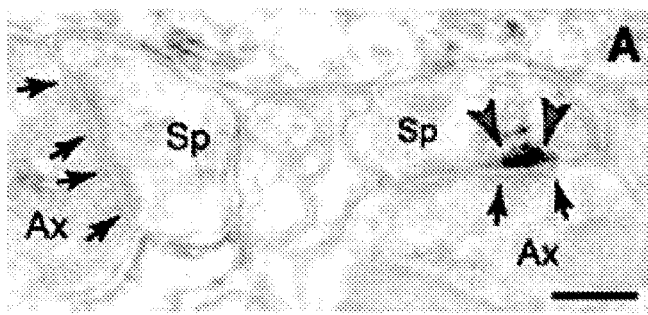
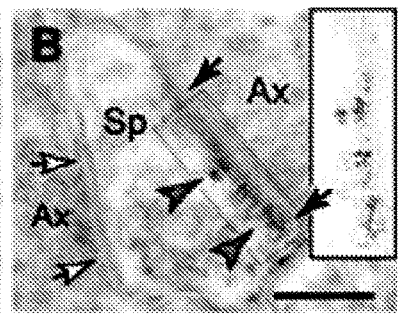
Fig. 2C
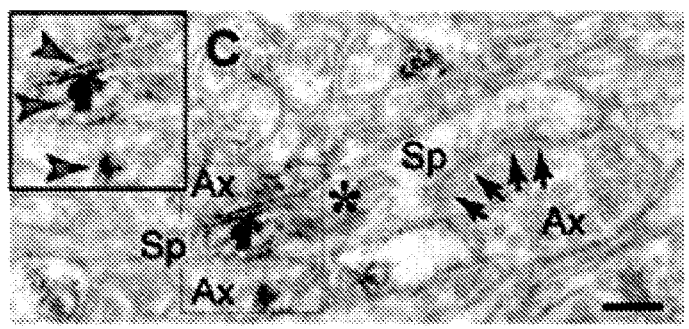
Fig. 2D
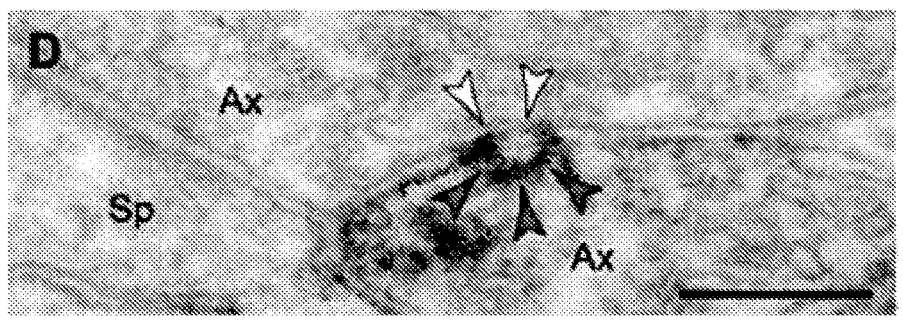
Fig. 2E
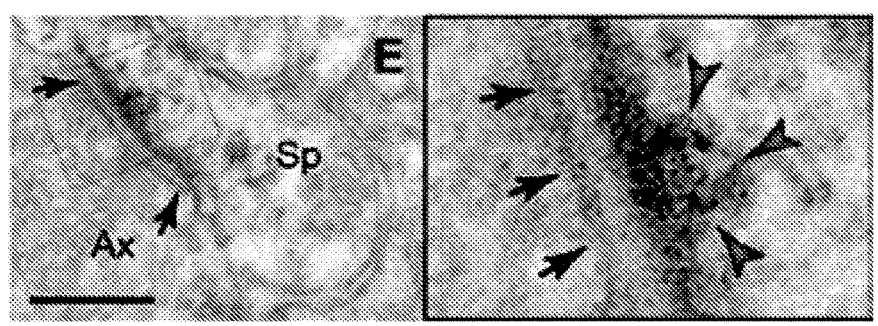

Fig. 3A
Fig. 3B
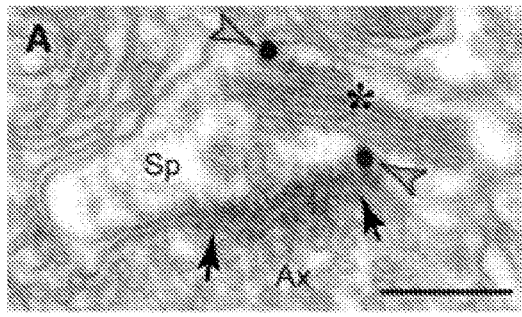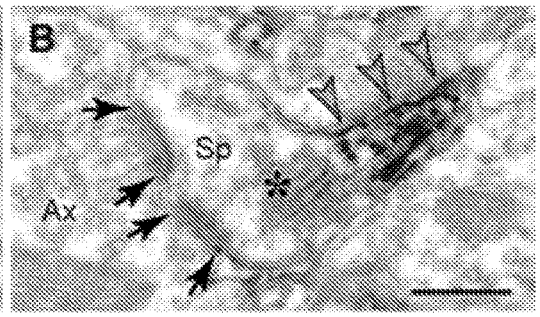
Fig. 3C
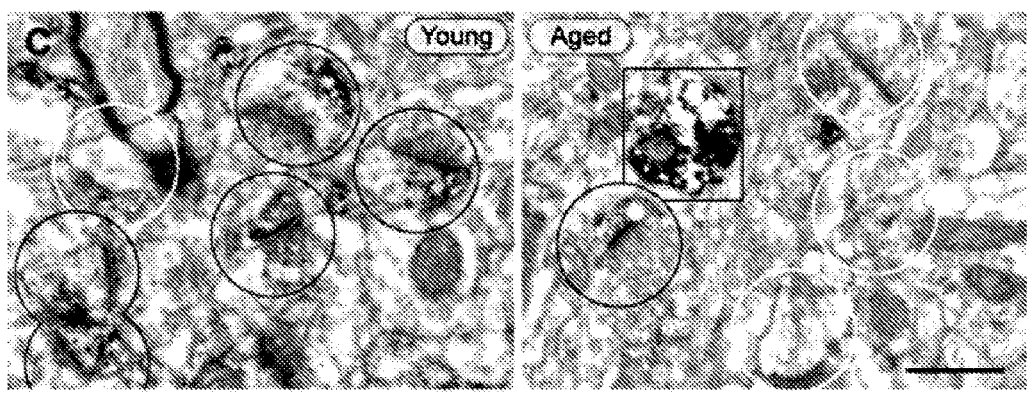
Fig. 3D
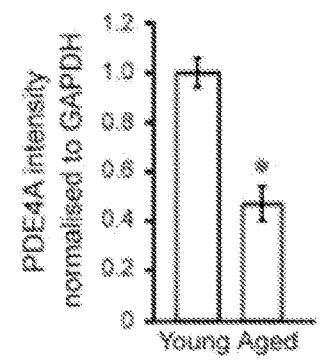

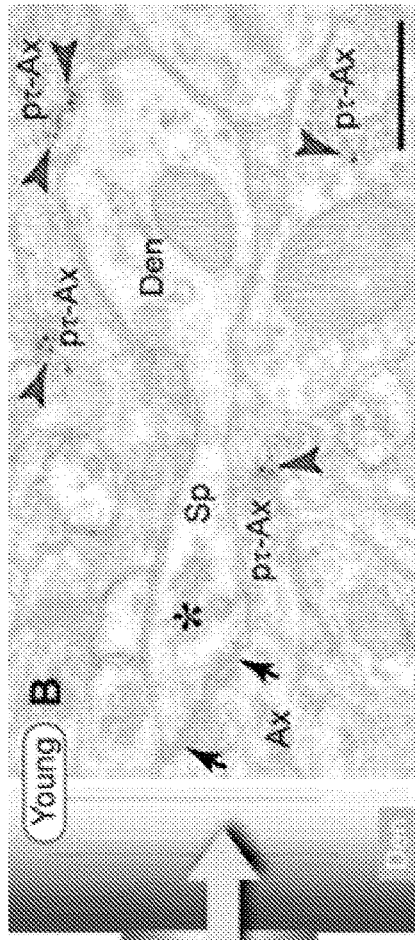
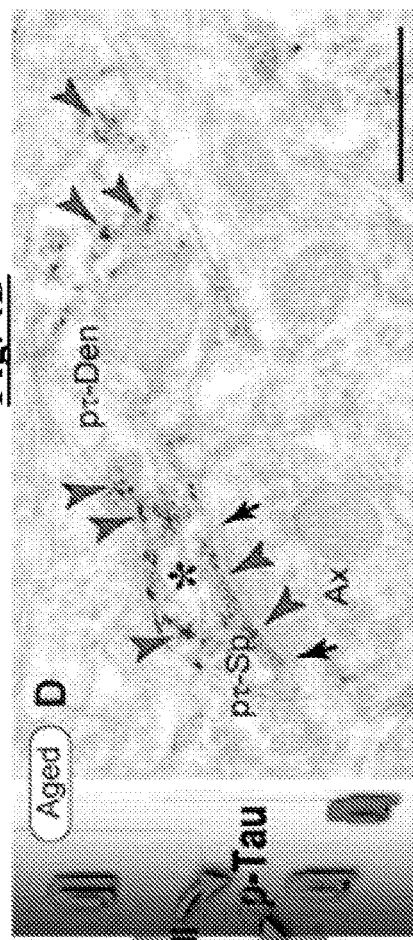
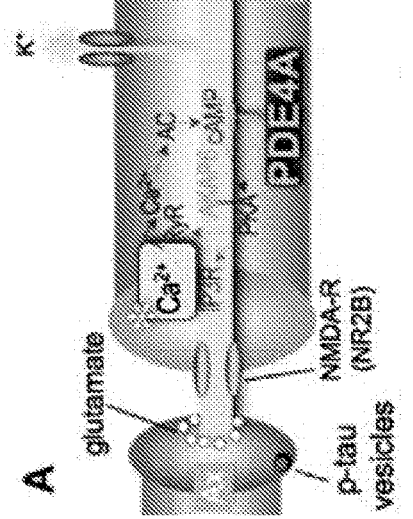
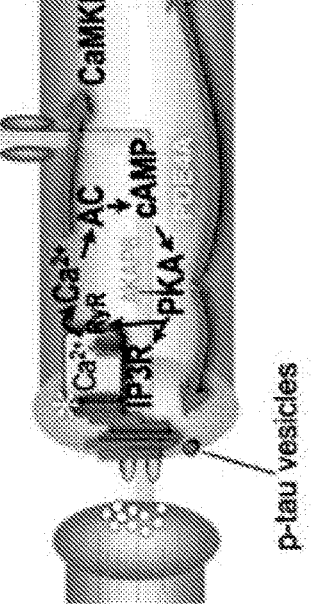
Fig. 4A
Fig. 4B
Fig. 4C
Fig. 4D

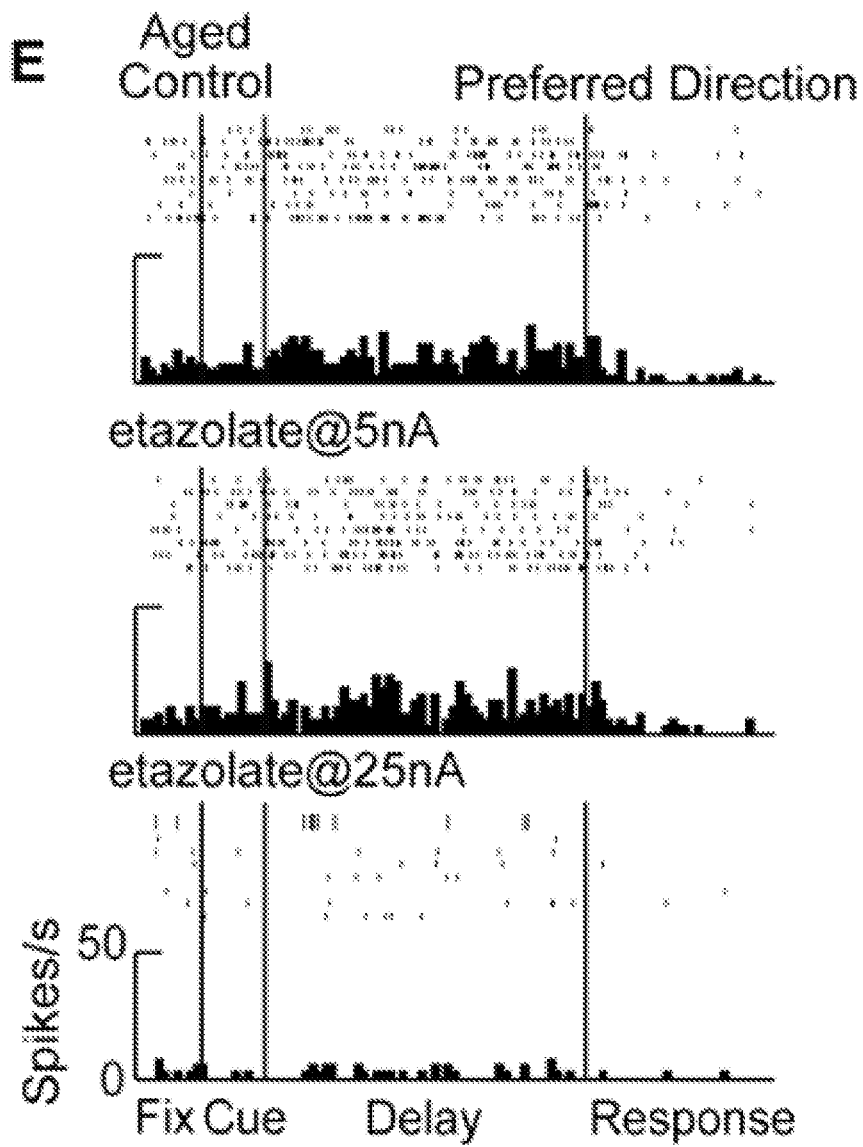

A. p-COXIV: Monkey PFC

B. ROS: Mouse PFC

A. α2A-AR are on PFC spines & dendrites near mitochondria

B. Chronic guanfacine improves cognition

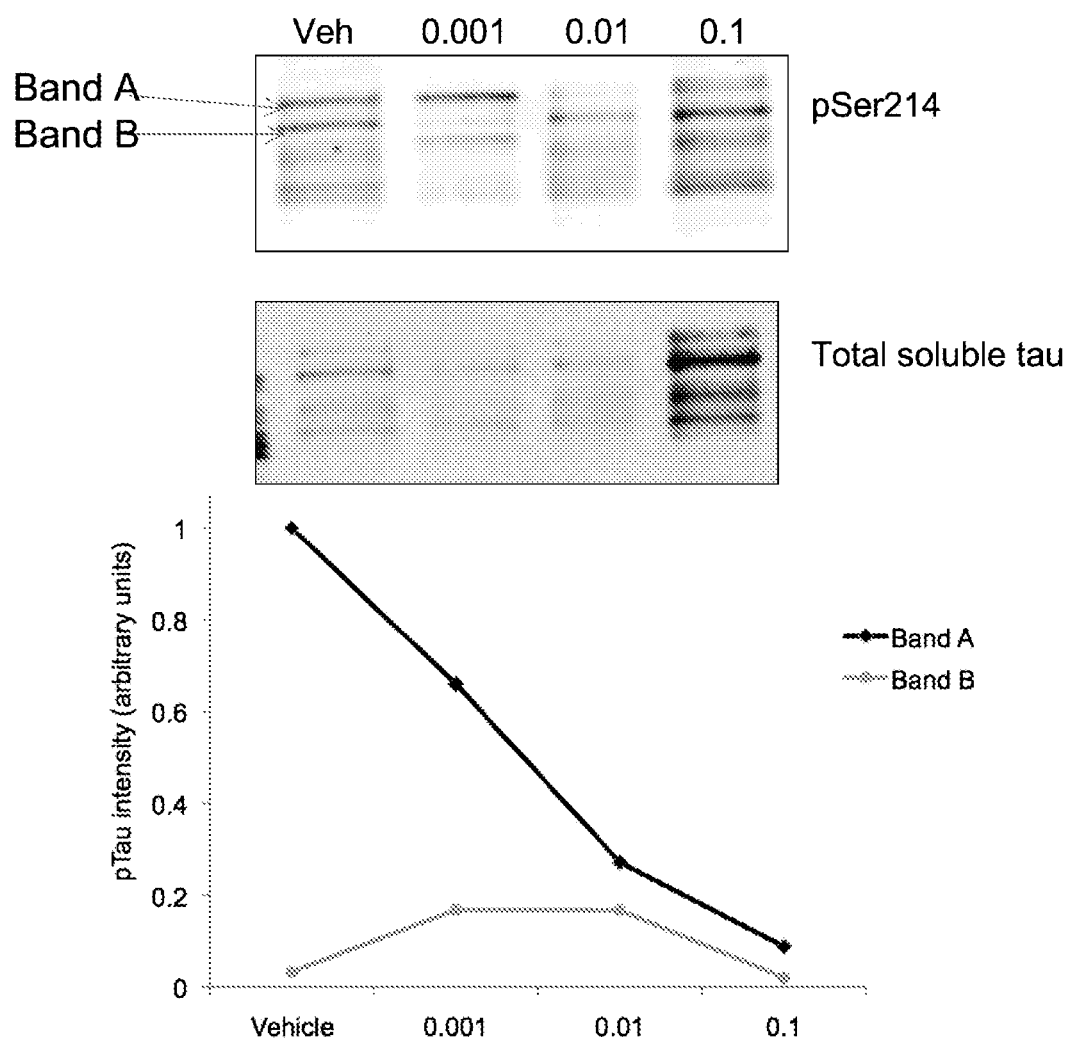

METHODS OF PREVENTING NEURODEGENERATION OF ASSOCIATION CORTEX IN A MAMMAL

CROSS-REFERENCE TO RELATED APPLICATIONS

The present application is a 35 U.S.C. § 371 national phase application from, and claims priority to, International Application No. PCT/US2015/063428, filed Dec. 2, 2015, and published under PCT Article 21(2) in English, which claims priority under 35 U.S.C. § 119(e) to U.S. Provisional Application No. 62/086,363, filed Dec. 2, 2014, all of which applications are incorporated herein by reference in their entireties.

STATEMENT REGARDING FEDERALLY SPONSORED RESEARCH OR DEVELOPMENT

This invention was made with government support under AG030004 and AG047744 awarded by National Institutes of Health. The government has certain rights in the invention.

BACKGROUND OF THE INVENTION

Amyloid plaques and neurofibrillary tangles (NFT) are hallmarks of pathology in neurodegenerative disorders such as Alzheimer's disease (AD) (Braak et al., 2011, J. Neuropathol. Exp. Neurol. 70:960). NFT arise from phosphorylation of tau protein by a variety of kinases, including cAMP-dependent protein kinase (PKA) (Jicha et al., 1999, J. Neurosci. 19:7486). Hyperphosphorylation induces aggregation of tau into paired helical filaments (PHF), which in humans and rhesus monkeys can progress to NFT formation.

In AD, NFT selectively form in association cortices with the more extensive corticocortical connections between pyramidal cells (Bussière et al., 2003, J. Comp. Neurol. 463:281), as in layer III of the dorsolateral prefrontal association cortex (dlPFC), which is afflicted quite early and extensively in AD (Pearson et al., 1985, Proc. Natl. Acad. Sci. USA 82:4531). The numbers of NFT in association cortex correlate with the severity of dementia (Giannakopoulos et al, 2003, neurology 60:1495-1500), indicating that these signs of degeneration are linked to cognitive dysfunction. In contrast, primary sensory cortices (e.g., visual area V1) are little affected even in late disease (Pearson et al., 1985, Proc. Natl. Acad. Sci. USA 82:4531; Lewis et al., 1987, J. Neurosci. 7:1799). Studies of the nonhuman primate dlPFC have shown that these layer III pyramidal cell circuits interconnect on long, thin spines with glutamate NMDA-NR2B receptor excitatory synapses, and are extensively modulated by feedforward cAMP-$Ca^{2+}$ signaling (Arnsten et al., 2012, Neuron 76:223).

Understanding why these circuits are selectively vulnerable to AD with advancing age is key to revealing disease etiology and thus developing strategies for intervention. Brains from individuals in their 40s and 50s displayed phosphorylated soluble tau in association cortex, indicating that the process may begin earlier than previously thought. Rodent AD models have provided a wealth of information regarding β-amyloid and tau signaling, but have not addressed this important issue, as rodents lack highly developed association cortices, and genetic alterations are introduced globally and do not mimic the pattern of pathology seen in humans (Platt et al., 2013, Biochim. Biophys. Acta 1832:1437).

Studies have shown evidence of mitochondrial dysfunction in AD, including reduced energy production and increases in reactive oxidation species (ROS) (Ferreira et al., 2010, Curr. Drug Targets 11:1193-1206). Excessive calcium release disrupts mitochondrial function (Mattson, 2010, Sci. Signal. 3:pe10; Camandola & Mattson, 2011, Biochim. Biophys. Acta:965-973), and recent findings suggest that increased cAMP-PKA activity with advancing age may also contribute to mitochondrial dysfunction. PKA phosphorylates cytochrome oxidase subunit IV (COXIV), which reduces ATP feedback and increases ROS production (Acin-Perez, et al., 2011, Cell Metab. 13:712-719).

There is a need in the art for novel methods of preventing or reducing risk of neurodegeneration of association cortex (or cortical degeneration) in a mammal in need thereof. Such methods may be used to prevent cognition loss in mammals that show no evident loss of cognitive abilities. The present invention fulfills these needs.

BRIEF SUMMARY OF THE INVENTION

The invention provides a method of preventing or reducing risk of cortical degeneration in a mammal in need thereof. The invention further provides a method of inhibiting or reversing formation of phosphorylated tau or COXIV in the prefrontal cortex of a mammal in need thereof.

In certain embodiments, the method comprises administering to the mammal a therapeutically effective amount of at least one α2A-adrenergic receptor agonist. In other embodiments, cortical degeneration is prevented or the risk thereof is reduced. In yet other embodiments, cognition in the mammal is preserved. In yet other embodiments, formation of phosphorylated tau or COXIV in the prefrontal cortex of the mammal is inhibited or reversed.

In certain embodiments, the agonist comprises at least one selected from the group consisting of guanfacine, brimonidine, guanabenz, guanoxabenz, a salt or solvate thereof, and mixtures thereof. In other embodiments, the agonist comprises at least one selected from the group consisting of clonidine, xylazine, dexmedetomidine, detomidine, medetomidine, a salt or solvate thereof, and mixtures thereof. In yet other embodiments, the agonist is administered to the mammal as part of a pharmaceutically acceptable composition.

In certain embodiments, the mammal does not have symptoms of a neurodegenerative disease or disorder. In other embodiments, the mammal has not been diagnosed with a neurodegenerative disease or disorder. In yet other embodiments, the mammal has symptoms of a neurodegenerative disease or disorder. In yet other embodiments, the mammal has been diagnosed with a neurodegenerative disease or disorder. In yet other embodiments, the mammal does not have a disease or disorder that is a risk factor for the development of dementia or other cognitive disorders. In yet other embodiments, the mammal has a disease or disorder that is a risk factor for the development of dementia or other cognitive disorders. In yet other embodiments, the mammal has not been diagnosed with a disease or disorder that is a risk factor for the development of dementia or other cognitive disorders. In yet other embodiments, the mammal has been diagnosed with a disease or disorder that is a risk factor for the development of dementia or other cognitive disorders. In yet other embodiments, the disease or disorder comprises at least one selected from the group consisting of Alzheimer's disease, Parkinson's disease, frontal temporal dementia, a tauopathy, chronic traumatic encephalopathy, traumatic brain injury, and mild cognitive impairment.

In certain embodiments, the mammal has a disease or disorder with cognitive symptoms. In other embodiments, the mammal does not have a disease or disorder with cognitive symptoms. In yet other embodiments, the mammal has not been diagnosed with a disease or disorder with cognitive symptoms. In yet other embodiments, the mammal has been diagnosed with a disease or disorder with cognitive symptoms. In yet other embodiments, the disease or disorder comprises at least one selected from the group consisting of major depressive disorder, anxiety disorders, multiple sclerosis, cancer, chemotherapy side effects, bipolar disorder, schizophrenia, diabetes, Lyme disease, and hypertension.

In certain embodiments, the disease or disorder affects or modulates cAMP-$Ca^{2+}$ release.

In certain embodiments, the administration of the agonist inhibits or reverses formation of phosphorylated tau in the prefrontal cortex of the mammal. In other embodiments, the administration of the agonist inhibits or reverses formation of phosphorylated COXIV in the prefrontal cortex of the mammal.

In certain embodiments, the agonist is formulated as part of an extended-release formulation. In other embodiments, the agonist is administered as a prodrug to the mammal. In yet other embodiments, the daily dose of agonist ranges from about 0.001 mg/kg/day to about 0.1 mg/kg/day. In yet other embodiments, the daily dose of agonist is about 0.01 mg/kg/day.

In certain embodiments, the mammal is a primate. In other embodiments, the primate is human.

In certain embodiments, the agonist is administered to the mammal by at least one route selected from the group consisting of inhalational, oral, rectal, vaginal, parenteral, topical, transdermal, pulmonary, intranasal, buccal, sublingual, ophthalmic, intrathecal, intravenous and intragastrical.

BRIEF DESCRIPTION OF THE DRAWINGS

For the purpose of illustrating the invention, there are depicted in the drawings certain embodiments of the invention. However, the invention is not limited to the precise arrangements and instrumentalities of the embodiments depicted in the drawings.

FIG. 1A: The aged dlPFC presented intense pS214-tau immunoreactivity along apical and basal pyramidal dendrites (arrowheads), and diffuse reactivity in the neuropil. FIG. 1B: In contrast, pS214-tau was not detected in aged monkey V1 (arrowheads point to dendrites for comparison). Scale bar, 20 μm. FIG. 1C: Immunoblots on heat-stable tau preparations from monkey dlPFC showed an increase with age of tau phosphorylation at Ser214 (left) and Thr231 (right). FIG. 1D: ImmunoEM demonstrated age-related aggregation of pS214-tau (red ovals) along dendritic microtubules (arrows). Ax, axon; Den, dendrite. Pseudocolored. Scale bar, 0.5 μm.

FIGS. 2A-2E are a series of images illustrating the ultrastructural localization of pS214-tau in monkey dlPFC. FIGS. 2A-2C: In aged spines, p-tau (red arrowheads) aggregated selectively over the PSD of asymmetric, glutamatergic-like synapses (black arrows)—symmetric synapses were not labeled (FIG. 2B, white arrows)—and the SA (FIG. 2C, asterisk). FIG. 2D: Axons in young dlPFC contained p-tau-reactive vesicles of 50 nm in diameter with clear lumen (red arrowheads) that fused with the axolemma to form exocytotic omega-shaped profiles (white arrowheads). FIG. 2E: In aged dlPFC, p-tau vesicular profiles were no longer present in axons but found in spines within the PSD of glutamatergic-like synapses (arrows). Ax, axon; Den, dendrite; Sp, spine. Pseudocolored. Scale bars, 200 nm.

FIGS. 3A-3G illustrate the finding that PDE4A decreases with age in PFC. FIGS. 3A-3B: In young monkey dlPFC, PDE4A (green arrowheads) was localized next to the SA (pseudocolored); immunogold and immunoperoxidase, respectively. FIG. 3C: PDE4A was widely expressed in layer III spines in young, but not in aged dlPFC (green circles, PDE4A-spines; white circles, unlabeled spines; green rectangle, PDE4A-dendrite). Scale bar, 0.5 μm. FIG. 3D: Immunoblot and quantification showing decreased PDE4A5 protein expression with age in monkey dlPFC; normalized to GAPDH; 7-11 yrs vs. 20-28 yrs: *$p<0.05$. FIG. 3E: Low doses of the PDE4 inhibitor etazolate (5-10 nA) decreased task-related firing of dlPFC neurons in young but not aged monkeys, while a high dose (25 nA) reduced firing in all neurons (n=39). Significant effects of etazolate dose (F=6.95, p=0.002) and age (F=12.27, p=0.001); significant changes from 0 nA: *$p<0.05$; *$p<0.009$; firing rates percentage young control. FIG. 3F: Quantification of PSD preparations from mouse frontal cortex showed significant decrease of PDE4A5 in the PSD fraction with age: $p<0.05$; (remains significant ($p<0.05$) when normalized by PSD95 levels to account for presumed spine loss). FIG. 3G: PDE4 inhibitor, rolipram, increased pS214-tau in mouse primary cortical neurons. Activation of PKA by forskolin (Fsk) produced a dose-related increase in pS214-tau (F(4, 60)=8.920, p<0.0001) that was significantly increased by rolipram (10 μM; F(1,60)=8.882, p=0.0042).

FIGS. 4A-4D are a series of non-limiting illustrations relating to age-related alterations in layer III corticocortical, network synapses in primate dlPFC. FIG. 4A: Schematic illustration of the young dlPFC, with PDE4A positioned to regulate feedforward cAMP-$Ca^{2+}$—$K^+$ signaling near glutamate synapses in dendritic spines. Sparse pS214-tau-immunoreactivity was found along microtubules in axons and dendrites, and there was evidence of pS214-tau vesicular trafficking between axons. FIG. 4B: Representative immunoEM of pS214-tau (red arrowheads) in young dlPFC. FIG. 4C: Schematic illustration of changes in aged dlPFC, with loss of PDE4A, dysregulation of cAMP-$Ca^{2+}$—$K^+$ signaling, and aggregation of pS214-tau in the PSD, the SA (asterisk) and along microtubules in distal dendrites. pS214-tau endoplasmic vesicles were seen in spines. FIG. 4D: Representative immunoEM of pS214-tau in aged dlPFC. Ax, axon; Den, dendrite; Sp, spine. Scale bars, 200 nm.

FIGS. 5A-5B: Graphs illustrate increases in pThr231 (FIG. 5A) and pSer214 (FIG. 5B) tau phosphorylation with age. Fitting to an exponential model showed a highly significant correlation of tau phosphorylation with age for both phosphorylation sites. Total heat-stable tau band intensity was normalized by total protein from the heat-stable preparation (FIG. 5C). This normalized total tau intensity was then used to normalize p-tau intensity to produce these graphs. FIG. 5C: To control for total soluble protein in the heat-stable extract, a separate gel was run in parallel and stained with Coomassie Blue and the major bands were quantified using Image J. The average intensity of these major species was used to normalize total tau band intensity. There was no overall reduction in soluble protein in aged tissue, therefore the decreased levels of soluble tau were not due to a general loss of soluble protein.

FIGS. 7A-7B: p-Tau aggregated along the microtubules of small caliber, high-order dendrites; cross section (FIG. 7A) and longitudinal section (FIG. 7B). A single microtubule may present intermittent reactivity along its length (red and white arrowheads point to p-tau-reactive and non-reactive microtubules/microtubule sections, respectively). Unlike asymmetric synapses on spines, the asymmetric synapse onto the dendrite in FIG. 7A (black arrows) is not labeled against p-tau. Ax, axon; Den, dendrite. Pseudocolored. Scale bars, 100 nm.

FIGS. 8A-8B: High-power electron micrographs demonstrating the selective accumulation of p-tau (red arrowheads) on the SA. The limiting membrane of the apparatus reticular cisterns (pseudocolored for clarity) is labeled, as is the plasma membrane and the post-synaptic membrane of the spine in FIG. 8B (red double arrowheads). Arrows point to asymmetric, glutamatergic-like synapses. Ax, axon; Sp, spine. Scale bars, 100 nm.

FIGS. 9A-9D: AKAP6 was selectively localized (orange arrowheads) on the SA, the extension of the dendrite's smooth reticulum into the spine; note the continuity of the SA with the SER of the parent dendrite in FIG. 9A (white arrowheads). FIGS. 9C-9D: Double immunoEM demonstrated AKAP6 (immunogold; orange arrowheads) colocalization with PDE4A (immunoperoxidase; green arrowheads) in the SA of dendritic spines. Thus, PDE4A is in a key subcellular location to regulate feedforward cAMP-$Ca^{2+}$ signaling in dlPFC spines. Arrows point to glutamatergic-like synapses. Ax, axon; Den, dendrite; Sp, spine. Scale bars, 200 nm.

FIGS. 10A-10E are a series of images and graphs illustrating the finding that the PDE4 inhibitor, etazolate, has more potent effects on dlPFC neurons of young than aged monkeys performing a spatial working memory task. FIG. 10A: The oculomotor delayed response (ODR) task, a test of spatial working memory used in the physiology experiments. The subject began a trial by fixating at the central spot (fixation period), whereupon a cue was illuminated for 0.5 sec (cue period) at one of eight peripheral targets. After the cue, a 2.5-sec delay period followed. The subject was required to maintain central fixation throughout both the cue presentation and the delay period. At the end of the delay, the fixation spot was extinguished, which instructed the monkey to make a memory guided saccade to the location where the cue had been shown prior to the delay period. A trial was considered successful if the subject's response was completed within 0.5 sec of the offset of the fixation spot, and within 2° around the correct cue location. The subject was rewarded with fruit juice immediately after every successful response. The position of the stimulus was randomized over trials (intertrial intervals (ITI) of 2 sec) such that it had to be remembered on a trial-by-trial basis. FIG. 10B: An example of a dlPFC "delay cell" with spatially tuned, persistent firing across the delay period, the neuronal representation of visual space. The yellow highlight indicates the preferred direction of this particular neuron; the gray shading shows the "antipreferred" direction. FIG. 10C: The recording site in the dlPFC in the caudal portion of the principal sulcus (PS) near the arcuate sulcus (AS). This is the dlPFC region that receives visual spatial information from parietal association cortex and is most needed for performance of the ODR task. FIG. 10D: An example of etazolate's effect on a dlPFC Delay cell from a young monkey (9 yrs). Etazolate (5 nA) significantly reduced delay-related firing compared to control conditions ($p<0.05$, one-way ANOVA). Only firing for the neuron's preferred direction is shown. FIG. 10E: An example of etazolate's effects on a dlPFC Delay cell from an aged monkey (21 yrs). Etazolate (5 nA) did not significantly alter delay-related firing compared to control conditions, while the higher etazolate dose (25 nA) significantly reduced firing ($p<0.05$, one-way ANOVA). Only firing for the neuron's preferred direction is shown.

FIG. 11A: Immunoblot showing the segregation of PDE4A isoforms throughout the stages of the PSD preparation process. The blot used 1 sample from a 6 month-old and 1 from a 24 month-old mouse. Only PDE4A5 was detectable in the Triton-insoluble PSD fraction. FIG. 11B: Immunoblots showing the data quantified in FIG. 3F. Blots depict Triton-insoluble PSD fraction staining for PDE4A5 (Abcam, ab14607), PDE4B (antibody was a kind gift from George Baillie, University of Glasgow), β-tubulin (Sigma) and PSD95 (EMD Millipore). Each band represented tissue pooled from 2 animals of the same age: n=4 pools per age group. FIG. 11C: PDE4A, PDE4B and PSD95 bands were quantified and normalized to β-tubulin to control for protein loading. PDE4A and PDE4B bands were further normalized with regards to PSD95 intensity to account for observed PSD loss. **$p<0.05$, remained significant ($p<0.05$) when also normalized by PSD95 levels. *$p<0.05$, significance was lost after correction for PSD95 intensity. Error bars show standard error of the mean.

ACCACAACAGCCTGCACGCA (SEQ ID NO: 1); Reverse pan PDE4A probe: TGCCAGCTCCGAATTGGT-GTTG (SEQ ID NO: 2).

Figure 14:
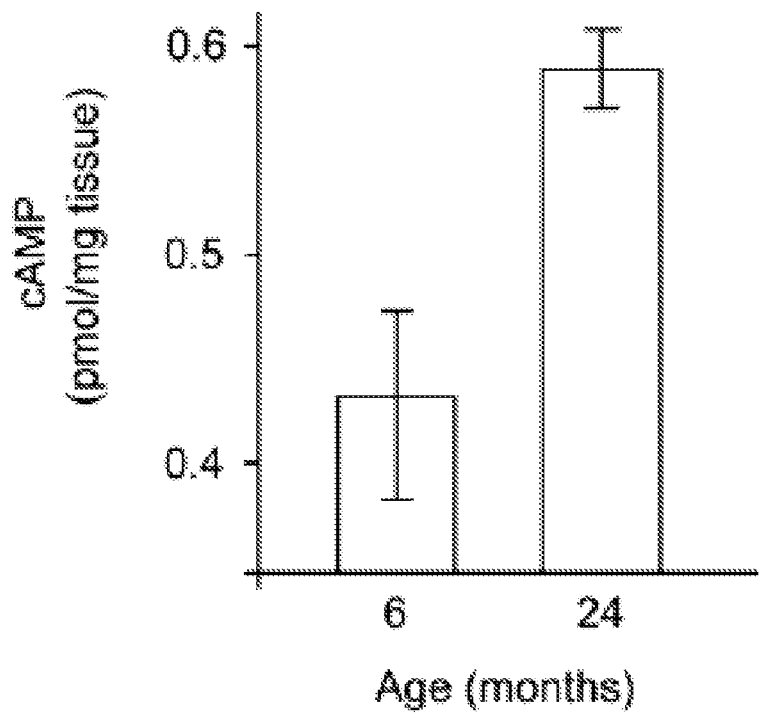

FIG. 14 is a bar graph illustrating cAMP in rat PFC as measured by ELISA. Rats were subject to focused microwave irradiation to inactivate phosphatase enzymes, and the cAMP ELISA performed according to manufacturer's instructions (Correlate-EIA Enzyme Immunoassay Kit, Assay Designs Inc). Aged rat medial PFC (24 months) had significantly higher cAMP levels than young adult medial PFC (6 months; p=0.0019, one way ANOVA, SYSTAT). These findings are consistent with reduced PDE4A in the synapses from aged rodent PFC. Error bars show standard error of the mean.

Figure 15:
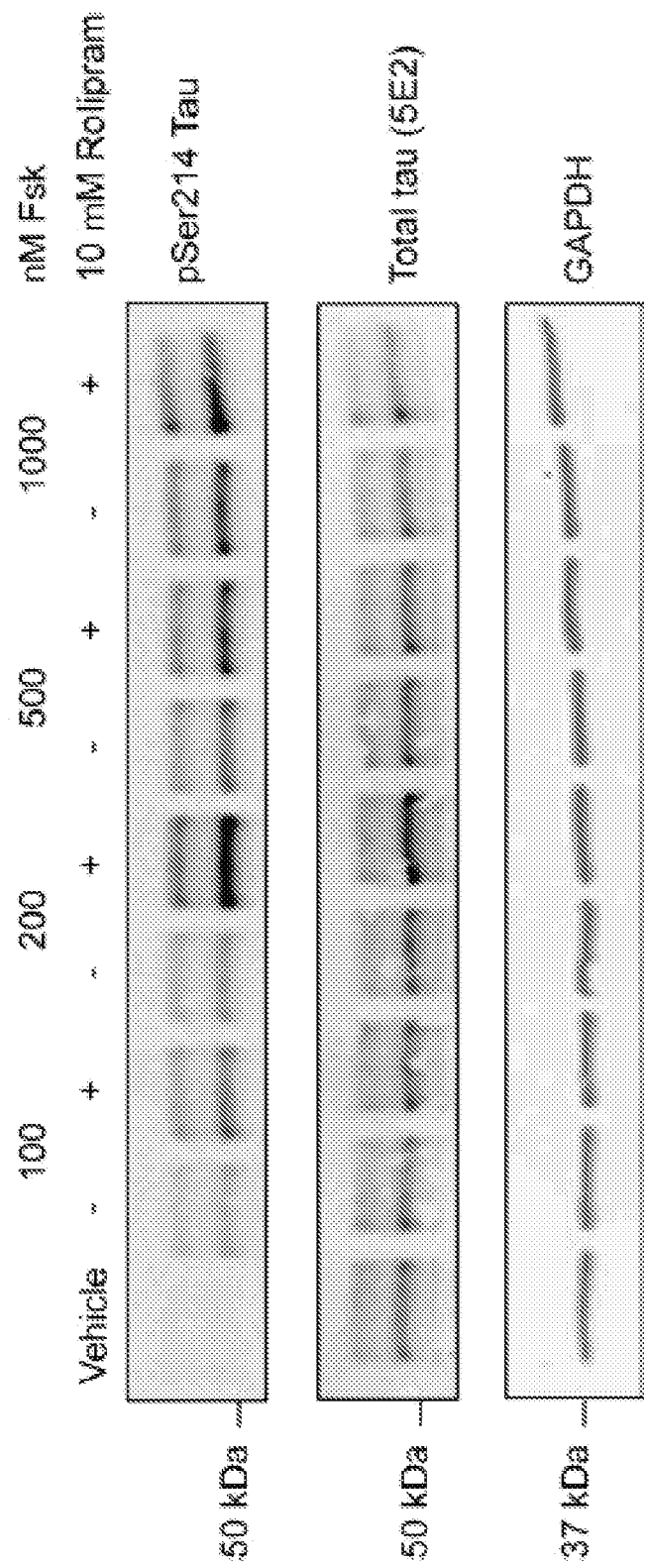

FIG. 15 is a series of immunoblots illustrating the effect of PDE4 inhibition on phosphorylation of tau at Serine 214. Sample immunoblot (one representative experiment of seven) depicting data summarized in FIG. 3G. Mouse primary cortical neurons between 7-11 days in vitro were preincubated with 10 μM rolipram or vehicle for 10 min, before being subjected to treatment with varying nM concentrations of forskolin (as indicated). Following this treatment, cells were lysed in 1% SDS with protease and phosphatase inhibitors (Complete Mini, Roche and PhosStop, Roche), and heated to 70° C. to prevent further phosphatase activity. Samples were quantified by BCA assay, and analyzed by imunoblotting. Blots were labeled for pSer214-tau (Abcam, 4846), total tau (EMD Millipore, clone 5E2) and GAPDH (Advanced Immunochemical, mAb 6C5). Bands were quantified using Image J, and total tau signals were normalized by GAPDH. p-Tau signals were then normalized to total tau signals.

Figure 16A:
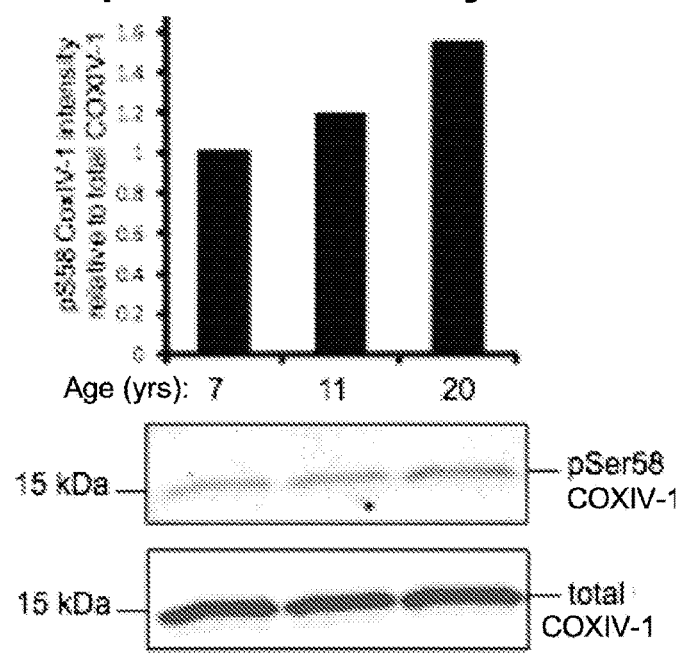
Figure 16B:
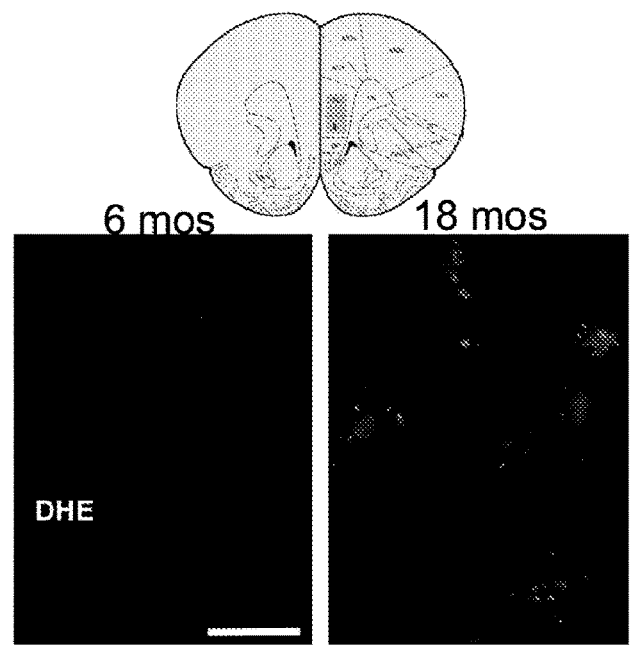

FIGS. 16A-16B illustrate mitochondrial changes with advancing age. FIG. 16A: PKA phosphorylation of COXIV-1 at pSer58 reduced ATP feedback and led to increased ROS production. Preliminary data showed increased phosphorylation of COXIV-1 at pSer58 with advancing age in the monkey dlPFC. FIG. 16B: ROS production in identified in mouse prefrontal cortical neurons of mice by injecting dihydroethidium (DHE), as it is specifically oxidized by superoxide to red fluorescent ethidium. Preliminary data indicated that there is more DHE present in the aging mouse (18 mos) medial PFC than in the same area in the 6 mos young adult, indicating elevated ROS levels with advancing age. Scale bar: 10 micrometers.

Figure 17A:
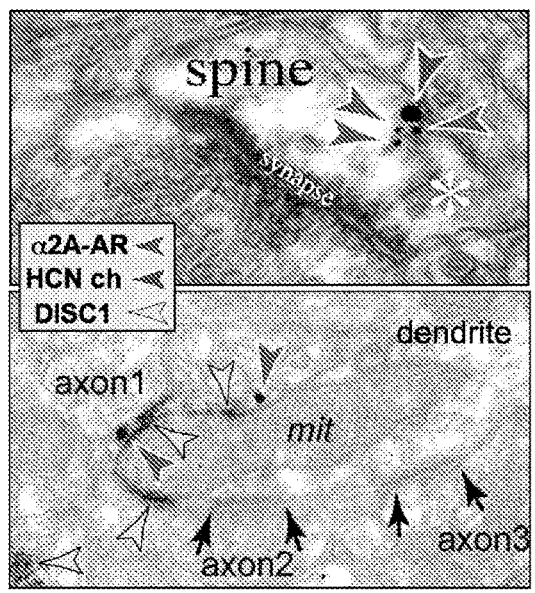
Figure 17B:
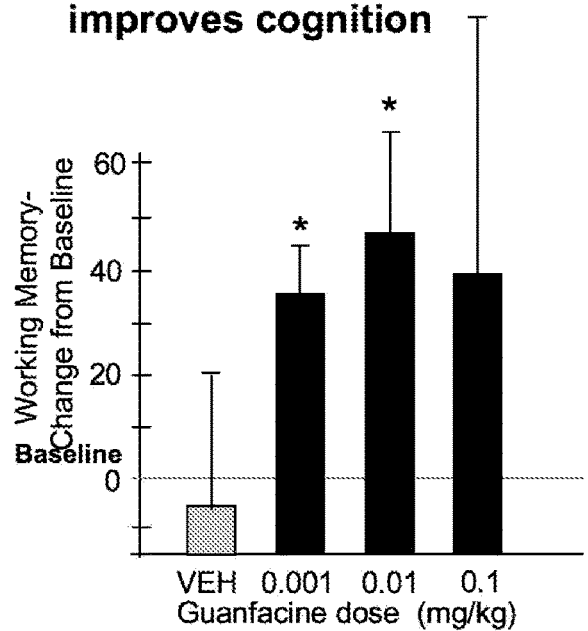

FIGS. 17A-17B illustrate the finding that chronic daily treatment with the $\alpha_{2A}$-adrenergic receptor (AR) agonist, guanfacine, reduces abnormal phosphorylation in the aged monkey dlPFC. FIG. 17A: Immunogold labeling of monkey dlPFC show that $\alpha_{2A}$-AR are positioned to inhibit cAMP signaling at key locations on dlPFC pyramidal cells. The upper panel shows $\alpha_{2A}$-AR (green arrow-heads) localized on spines near the synapse, often next to $K^+$ channels (e.g. HCN channels, red arrowhead), and near the spine apparatus (asterisk)). The lower panel shows $\alpha_{2A}$-AR on a dendrite near mitochondria; mitochondria show typical labeling with DISC1 (yellow arrowheads). Axon 1 is likely an NE axon; $\alpha_{2A}$-AR can be found on at these traditional, presynaptic locations as well (mit=mitochondrion). FIG. 17B: Daily treatment with guanfacine (0.001 or 0.01 mg/kg) for 6 months significantly improved working memory performance in aged monkeys (18-28 yrs) compared to their performance at baseline; the effects of the highest guanfacine dose (0.1 mg/kg) were highly variable and thus not significant. No improvement was observed with chronic vehicle treatment (n=4 or 5).

FIG. 18 is a set of immunoblots and a graph illustrating the finding that chronic daily treatment with the $\alpha_{2A}$-AR agonist, guanfacine, reduces abnormal phosphorylation of tau in the aged monkey dlPFC. Chronic guanfacine treatment (0.001-0.1 mg/kg) for 6 mos produced a dose-related reduction in p-S214 expression in the aged monkey dlPFC compared to chronic vehicle treatment (n=1).

Figure 19:
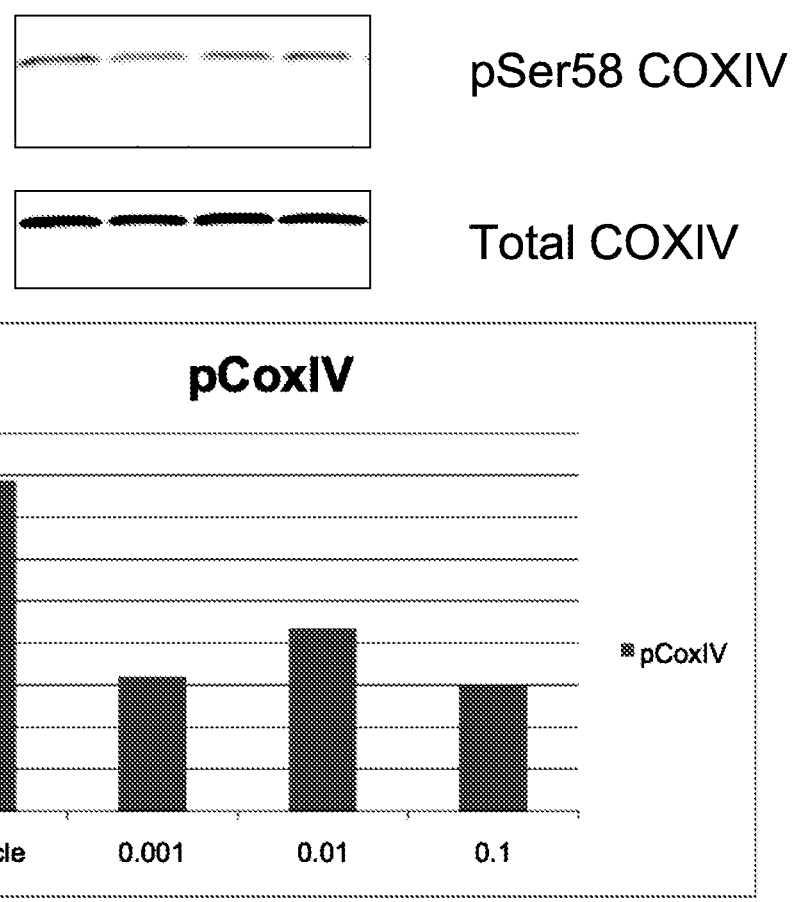

FIG. 19 is a set of immunoblots and a bar graph illustrating that chronic daily treatment with the $\alpha_{2A}$-AR agonist, guanfacine, reduces abnormal phosphorylation of COXIV in the aged monkey dlPFC. Chronic guanfacine treatment (0.001-0.1 mg/kg) for 6 mos decreased phospho-COXIV-1 expression (p-S58) in the aged monkey dlPFC compared to chronic vehicle treatment (n=1).

Figure 20A:
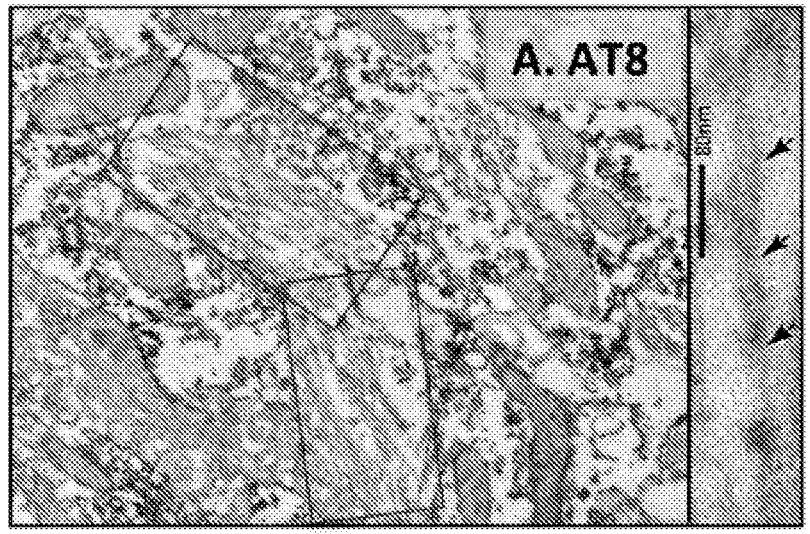
Figure 20B:
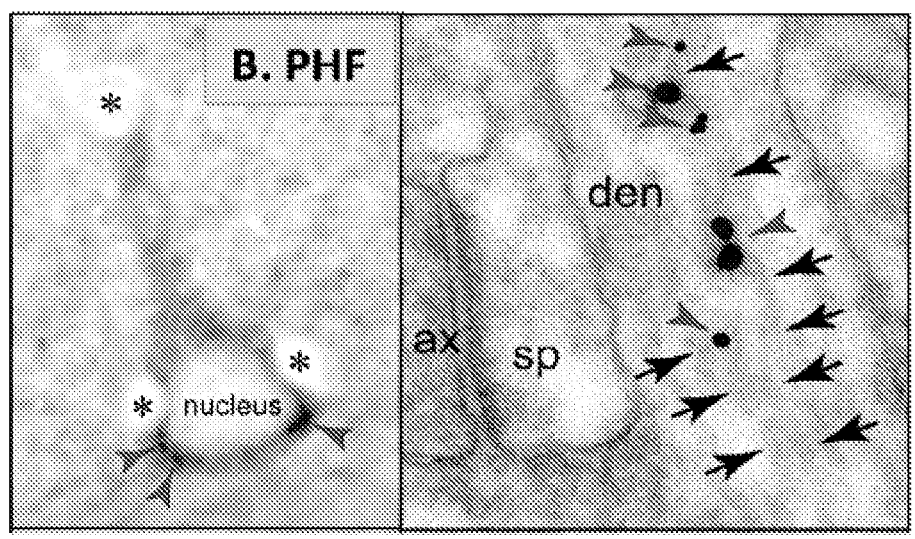

FIGS. 20A-20B are a set of images illustrating the presence of neurofibrillary tangles (NFTs) within neurons in the entorhinal association cortex of a very old (33 yo) rhesus monkey. FIG. 20A: NFTs (within red rectangles) were stained with the AT8 antibody commonly used to diagnose AD; the high magnification shown in the right image shows that the periodicity of the helix is consistent with that seen in NFTs in humans. FIG. 20B: The tissue was stained with an antibody that recognizes the paired helical filaments (PHF) of hyperphosphorylated tau that make up NFTs. The PHF staining at low magnification (light microscope, left image) showed aggregation in the cell body near the nucleus, and nearby autophagic vacuoles (*) that are often associated with beta amyloid accumulation. Higher magnification (electron micrograph, right image) showed that PHF also collect in dendrites. These are the first definitive demonstration that NFTs develop with extreme age in the rhesus monkey.

DETAILED DESCRIPTION OF THE INVENTION

The present invention relates to the unexpected discovery that chronic inhibition of cAMP-PKA signaling with an $\alpha_{2A}$ adrenergic receptor ($\alpha_{2A}$ AR) agonist inhibits phosphorylation of tau, thus reducing risk of degeneration in the association cortex. In one aspect, the invention includes a method of preventing or reducing risk of neurodegeneration of association cortex (or cortical degeneration) in a mammal in need thereof. In another aspect, the invention includes a method of inhibiting or reversing formation of phosphorylated tau or COXIV in the prefrontal cortex of a mammal in need thereof. In certain embodiments, the mammal is administered low doses of an $\alpha_{2A}$-adrenergic receptor agonist, thereby preventing or reducing risk of cortical degeneration in the mammal, even in those mammals that show no evident loss in cognitive abilities.

As demonstrated herein, cAMP-dependent protein kinase (PKA) tau phosphorylation increases with age in monkey prefrontal association cortex, and targets spine synapses and the $Ca^{2+}$-storing spine apparatus, including vesicular trafficking in spines. These events are mirrored by loss of PDE4A from the spine apparatus, consistent with increase in cAMP-$Ca^{2+}$ signaling in aging spines. Phosphorylated tau was not detected in primary visual cortex, which is little affected in AD. These data indicate that cAMP-$Ca^{2+}$ signaling mechanisms needed for flexibly modulating network strength in young association cortex confer vulnerability to degeneration when dysregulated with advancing age.

In one aspect, the present study revealed age-related increase in p-tau and reduction in PDE4A in pyramidal cell network synapses in primate association cortex (FIG. 4). The vast expansion of such connections on dendritic spines in primate evolution may magnify this process in human cortex and lead to sufficient phosphorylation to cause fibrillation, NFT formation and neuronal degeneration. Indeed, there is evidence of early stages of NFT formation in the extremely aged rhesus monkey association cortex as well (FIGS. 20A-20B). The discovery of p-tau aggregation at the spine post-synaptic membrane in aged primate dlPFC indicates that p-tau may interfere with synaptic transmission and receptor trafficking in pyramidal cell networks as part of the normal aging process, which may be exacerbated in those with tau mutations. In addition, the discovery of p-tau in trafficking vesicles provides a possible mechanism for trans-neuronal spread, which has never been shown in normal, aging brain. Because p-tau aggregates only in asymmetric axospinous synapses in the aged dlPFC, it further illuminates how degeneration could specifically target highly evolved glutamate pyramidal cell circuits with extensive connections on spines. As cAMP-$Ca^{2+}$ signaling is increased in PFC following psychological distress or traumatic brain injury, these data also may help to explain how exposure to psychological or physical trauma exacerbates the degenerative process. The loss of PDE4A from the SA may also aggravate p-tau accumulation in distal dendrites, as large increases in $Ca^{2+}$ release from the SA can spread to SER of the parent dendrite. Increased p-tau, especially in thin, highly branched dendrites, may cause steric hindrance that interferes with intracellular transport, including interference with APP trafficking that can increase production of Aβ. As Aβ oligomers drive intracellular $Ca^{2+}$ release, this cycle could propel the degenerative process. Tau phosphorylation in humans begins relatively early in the aging process, suggesting that interventions need to be initiated at younger ages. The current study demonstrates that the aging monkey can serve as an important animal model for understanding the molecular events that render the association cortices especially vulnerable to degeneration, and an opportunity to test agents that may slow or prevent this process by compensating for PDE4A dysregulation of cAMP signaling in dendritic spines.

Definitions

As used herein, each of the following terms has the meaning associated with it in this section.

Unless defined otherwise, all technical and scientific terms used herein generally have the same meaning as commonly understood by one of ordinary skill in the art to which this invention belongs. Generally, the nomenclature used herein and the laboratory procedures in cell culture, molecular genetics, organic chemistry, and peptide chemistry are those well known and commonly employed in the art.

As used herein, the articles "a" and "an" refer to one or to more than one (i.e. to at least one) of the grammatical object of the article. By way of example, "an element" means one element or more than one element.

As used herein, the term "about" is understood by persons of ordinary skill in the art and varies to some extent on the context in which it is used. As used herein when referring to a measurable value such as an amount, a temporal duration, and the like, the term "about" is meant to encompass variations of ±20% or ±10%, more preferably ±5%, even more preferably ±1%, and still more preferably ±0.1% from the specified value, as such variations are appropriate to perform the disclosed methods.

As used herein, the term "AD" refers to Alzheimer's disease.

As used herein, the term "AR" refers to adrenergic receptor or adrenoreceptor.

As used herein, the term "AS" refers to arcuate sulcus.

As used herein, the term "cAMP" refers to cyclic adenosine monophosphate.

As used herein, the term "composition" or "pharmaceutical composition" refers to a mixture of at least one compound useful within the invention with a pharmaceutically acceptable carrier. The pharmaceutical composition facilitates administration of the compound to a patient. Multiple techniques of administering a compound exist in the art including, but not limited to, intravenous, oral, aerosol, parenteral, ophthalmic, pulmonary and topical administration.

As used herein, the term "COXIV" refers to cytochrome oxidase subunit IV.

As used herein, the term "dlPFC" refers to dorsolateral prefrontal association cortex.

As used herein, the terms "effective amount," "pharmaceutically effective amount" and "therapeutically effective amount" refer to a nontoxic but sufficient amount of an agent to provide the desired biological result. That result may be reduction and/or alleviation of the signs, symptoms, or causes of a disease, or any other desired alteration of a biological system. An appropriate therapeutic amount in any individual case may be determined by one of ordinary skill in the art using routine experimentation.

"Instructional material," as that term is used herein, includes a publication, a recording, a diagram, or any other medium of expression that may be used to communicate the usefulness of the compounds of the invention. In some instances, the instructional material may be part of a kit useful for effecting alleviating or treating the various diseases or disorders recited herein. Optionally, or alternately, the instructional material may describe one or more methods of alleviating the diseases or disorders in a cell or a tissue of a mammal. The instructional material of the kit may, for example, be affixed to a container that contains the compounds of the invention or be shipped together with a container that contains the compounds. Alternatively, the instructional material may be shipped separately from the container with the intention that the recipient uses the instructional material and the compound cooperatively. For example, the instructional material is for use of a kit; instructions for use of the compound; or instructions for use of a formulation of the compound.

As used herein, the term "IP3R" refers to inositol tris-phosphate receptor.

As used herein, the term "ITI" refers to intertribal interval(s).

As used herein, the term "NFT" refers to neurofibrillary tangles.

As used herein, the term "patient," "individual" or "subject" refers to a human or a non-human mammal. Non-human mammals include, for example, livestock and pets, such as ovine, bovine, porcine, canine, feline and murine mammals. Preferably, the patient, individual or subject is human.

As used herein, the term "pharmaceutically acceptable" refers to a material, such as a carrier or diluent, which does not abrogate the biological activity or properties of the compound, and is relatively non-toxic, i.e., the material may be administered to an individual without causing undesirable biological effects or interacting in a deleterious manner with any of the components of the composition in which it is contained.

As used herein, the term "pharmaceutically acceptable carrier" means a pharmaceutically acceptable material, composition or carrier, such as a liquid or solid filler, stabilizer, dispersing agent, suspending agent, diluent, excipient, thickening agent, solvent or encapsulating material, involved in carrying or transporting a compound useful within the invention within or to the patient such that it may perform its intended function. Typically, such constructs are carried or transported from one organ, or portion of the body, to another organ, or portion of the body. Each carrier must be "acceptable" in the sense of being compatible with the other ingredients of the formulation, including the compound useful within the invention, and not injurious to the patient. Some examples of materials that may serve as pharmaceutically acceptable carriers include: sugars, such as lactose, glucose and sucrose; starches, such as corn starch and potato starch; cellulose, and its derivatives, such as sodium carboxymethyl cellulose, ethyl cellulose and cellulose acetate; powdered tragacanth; malt; gelatin; talc; excipients, such as cocoa butter and suppository waxes; oils, such as peanut oil, cottonseed oil, safflower oil, sesame oil, olive oil, corn oil and soybean oil; glycols, such as propylene glycol; polyols, such as glycerin, sorbitol, mannitol and polyethylene glycol; esters, such as ethyl oleate and ethyl laurate; agar; buffering agents, such as magnesium hydroxide and aluminum hydroxide; surface active agents; alginic acid; pyrogen-free water; isotonic saline; Ringer's solution; ethyl alcohol; phosphate buffer solutions; and other non-toxic compatible substances employed in pharmaceutical formulations. As used herein, "pharmaceutically acceptable carrier" also includes any and all coatings, antibacterial and antifungal agents, and absorption delaying agents, and the like that are compatible with the activity of the compound useful within the invention, and are physiologically acceptable to the patient. Supplementary active compounds may also be incorporated into the compositions. The "pharmaceutically acceptable carrier" may further include a pharmaceutically acceptable salt or solvate of the compound useful within the invention. Other additional ingredients that may be included in the pharmaceutical compositions used in the practice of the invention are known in the art and described, for example in Remington's Pharmaceutical Sciences (Genaro, Ed., Mack Publishing Co., 1985, Easton, Pa.), which is incorporated herein by reference.

As used herein, the language "pharmaceutically acceptable salt" refers to a salt of the administered compound prepared from pharmaceutically acceptable non-toxic acids and bases, including inorganic acids, inorganic bases, organic acids, inorganic bases, solvates, hydrates, and clathrates thereof. Suitable pharmaceutically acceptable acid addition salts may be prepared from an inorganic acid or from an organic acid. Examples of inorganic acids include sulfate, hydrogen sulfate, hydrochloric, hydrobromic, hydriodic, nitric, carbonic, sulfuric, and phosphoric acids (including hydrogen phosphate and dihydrogen phosphate). Appropriate organic acids may be selected from aliphatic, cycloaliphatic, aromatic, araliphatic, heterocyclic, carboxylic and sulfonic classes of organic acids, examples of which include formic, acetic, propionic, succinic, glycolic, gluconic, lactic, malic, tartaric, citric, ascorbic, glucuronic, maleic, fumaric, pyruvic, aspartic, glutamic, benzoic, anthranilic, 4-hydroxybenzoic, phenylacetic, mandelic, embonic (pamoic), methanesulfonic, ethanesulfonic, benzenesulfonic, pantothenic, trifluoromethanesulfonic, 2-hydroxyethanesulfonic, p-toluenesulfonic, sulfanilic, cyclohexylaminosulfonic, stearic, alginic, β-hydroxybutyric, salicylic, galactaric and galacturonic acid. Suitable pharmaceutically acceptable base addition salts of compounds of the invention include, for example, metallic salts including alkali metal, alkaline earth metal and transition metal salts such as, for example, calcium, magnesium, potassium, sodium and zinc salts. Pharmaceutically acceptable base addition salts also include organic salts made from basic amines such as, for example, N,N'-dibenzylethylene-diamine, chloroprocaine, choline, diethanolamine, ethylenediamine, meglumine (N-methylglucamine) and procaine. All of these salts may be prepared from the corresponding compound by reacting, for example, the appropriate acid or base with the compound.

As used herein, the term "PKA" refers to cAMP-dependent protein kinase.

As used herein, the term "polypeptide" refers to a polymer composed of amino acid residues, related naturally occurring structural variants, and synthetic non-naturally occurring analogs thereof linked via peptide bonds. Synthetic polypeptides may be synthesized, for example, using an automated polypeptide synthesizer. As used herein, the term "protein" typically refers to large polypeptides. As used herein, the term "peptide" typically refers to short polypeptides. Conventional notation is used herein to represent polypeptide sequences: the left-hand end of a polypeptide sequence is the amino-terminus, and the right-hand end of a polypeptide sequence is the carboxyl-terminus.

As used herein, amino acids are represented by the full name thereof, by the three letter code corresponding thereto, or by the one-letter code corresponding thereto, as indicated below:

| Full Name | Three-Letter Code | One-Letter Code |
|---|---|---|
| Aspartic Acid | Asp | D |
| Glutamic Acid | Glu | E |
| Lysine | Lys | K |
| Arginine | Arg | R |
| Histidine | His | H |
| Tyrosine | Tyr | Y |
| Cysteine | Cys | C |
| Asparagine | Asn | N |
| Glutamine | Gln | Q |
| Serine | Ser | S |
| Threonine | Thr | T |
| Glycine | Gly | G |
| Alanine | Ala | A |
| Valine | Val | V |
| Leucine | Leu | L |
| Isoleucine | Ile | I |
| Methionine | Met | M |
| Proline | Pro | P |
| Phenylalanine | Phe | F |
| Tryptophan | Trp | W |

As used herein, the term "prevent" or "prevention" means no disorder or disease development if none had occurred, or no further disorder or disease development if there had already been development of the disorder or disease. Also considered is the ability of one to prevent some or all of the symptoms associated with the disorder or disease.

As used herein, the term "PS" refers to principal sulcus.

As used herein, the term "PSD" refers to post-synaptic density.

As used herein, the term "SA" refers to spine apparatus.

As used herein, the term "SER" refers to smooth endoplasmic reticulum.

As used herein, the term "solvate" comprises a complex of a molecule with a solvent, such as but not limited to water, methanol, ethanol, 1-propanol, 2-propanol, DMSO, DMF, acetone and the like.

As used herein, the term "treatment" or "treating" is defined as the application or administration of a therapeutic agent, i.e., a compound useful within the invention (alone or in combination with another pharmaceutical agent), to a patient, or application or administration of a therapeutic agent to an isolated tissue or cell line from a patient (e.g., for diagnosis or ex vivo applications), who has a disease or disorder, a symptom of a disease or disorder or the potential to develop a disease or disorder, with the purpose to cure, heal, alleviate, relieve, alter, remedy, ameliorate, improve or affect the disease or disorder, the symptoms of the disease or disorder, or the potential to develop the disease or disorder. Such treatments may be specifically tailored or modified, based on knowledge obtained from the field of pharmacogenomics.

Ranges: throughout this disclosure, various aspects of the invention can be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 2.7, 3, 4, 5, 5.3, and 6. This applies regardless of the breadth of the range.

Compounds

The compounds useful within the invention may be synthesized using techniques well-known in the art of organic synthesis.

In certain embodiments, the compound useful within the invention is an $\alpha_{2A}$-adrenergic receptor ($\alpha_{2A}$-AR) agonist (also known as an $\alpha_{2A}$-adrenoreceptor agonist).

In certain embodiments, the compound is a selective agonist for the $\alpha_{2A}$-adrenergic receptor at a post-synaptic site in cortex. In yet other embodiments, the compound is at least 3 times more selective for the $\alpha_{2A}$-adrenergic receptor at a post-synaptic site in cortex as compared to at least one other compound that acts at at least one other receptor at a post-synaptic site in cortex. In yet other embodiments, the compound is at least 10 times more selective for the $\alpha_{2A}$-adrenergic receptor at a post-synaptic site in cortex as compared to at least one other compound that acts at at least one other receptor at a post-synaptic site in cortex. In yet other embodiments, the compound is at least 30 times more selective for the $\alpha_{2A}$-adrenergic receptor at a post-synaptic site in cortex as compared to at least one other compound that acts at at least one other receptor at a post-synaptic site in cortex. In yet other embodiments, the compound is at least 100 times more selective for the $\alpha_{2A}$-adrenergic receptor at a post-synaptic site in cortex as compared to at least one other compound that acts at at least one other receptor at a post-synaptic site in cortex. In yet other embodiments, the compound is at least 300 times more selective for the α2A-adrenergic receptor at a post-synaptic site in cortex as compared to at least one other compound that acts at at least one other receptor at a post-synaptic site in cortex. In yet other embodiments, the compound is at least 1,000 times more selective for the α2A-adrenergic receptor at a post-synaptic site in cortex as compared to at least one other compound that acts at at least one other receptor at a post-synaptic site in cortex.

In certain embodiments, the selectivity for the α2A-adrenergic receptor over at least one other receptor is determined based on the conformations of the receptors as they exist in a post-synaptic, cortical membrane.

In certain embodiments, the compound is a selective agonist for the $\alpha_{2A}$-adrenergic receptor over at least one other receptor present in a post-synaptic site in cortex. In yet other embodiments, the compound is at least 3 times selective for the $\alpha_{2A}$-adrenergic receptor over at least one other receptor present in a post-synaptic membrane in cortex. In yet other embodiments, the compound is at least 10 times selective for the $\alpha_{2A}$-adrenergic receptor over at least one other receptor present in a post-synaptic membrane in cortex. In yet other embodiments, the compound is at least 30 times selective for the $\alpha_{2A}$-adrenergic receptor over at least one other receptor present in a post-synaptic membrane in cortex. In yet other embodiments, the compound is at least 100 times selective for the $\alpha_{2A}$-adrenergic receptor over at least one other receptor present in a post-synaptic membrane in cortex. In yet other embodiments, the compound is at least 300 times selective for the $\alpha_{2A}$-adrenergic receptor over at least one other receptor present in a post-synaptic membrane in cortex. In yet other embodiments, the compound is at least 1,000 times selective for the $\alpha_{2A}$-adrenergic receptor over at least one other receptor present in a post-synaptic membrane in cortex.

In certain embodiments, the selectivity for the $\alpha_{2A}$-adrenergic receptor over at least one other receptor present in cortex is determined based on the conformations of the receptors as they exist in a post-synaptic membrane in cortex.

In certain embodiments, non-limiting examples of compounds useful within the invention include: guanfacine (also known as N-(diaminomethylidene)-2-(2,6-dichlorophenyl)acetamide); brimonidine (also known as UK 14,304 (5-bromo-N-(2-imidazolin-2-yl)-6-quinoxalinamine, or 5-bromo-N-(4,5-dihydro-1H-imidazol-2-yl)-6-quinoxalinamine; guanabenz (also known as 2-(2,6-dichlorobenzylidene)hydrazinecarboximidamide); guanoxabenz (also known as 2-{[(2,6-dichlorophenyl)methylidene]amino}-1-hydroxyguanidine); a salt or solvate thereof and mixtures thereof.

In certain embodiments, non-limiting examples of compounds useful within the invention include: clonidine (also known as N-(2,6-dichlorophenyl)-4,5-dihydro-1H-imidazol-2-amine); xylazine (also known as N-(2,6-Dimethylphenyl)-5,6-dihydro-4H-1,3-thiazin-2-amine); dexmedetomidine (also known as (S)-4-[1-(2,3-Dimethylphenyl)ethyl]-3H-imidazole); detomidine (also known as 4-[(2,3-dimethylphenyl)methyl]-3H-imidazole); medetomidine (also known as (RS)-4-[1-(2,3-dimethylphenyl)ethyl]-3H-imidazole); a salt or solvate thereof and mixtures thereof.

The invention also contemplates the use of a prodrug of an $\alpha_{2A}$-adrenergic receptor agonist. In certain embodiments, the prodrug has improved bioavailability, pharmacokinetics and/or pharmacodynamics as compared to the corresponding $\alpha_{2A}$-adrenergic receptor agonist. In other embodiments, the prodrug has decreased in vivo toxicity as compared to the corresponding $\alpha_{2A}$-adrenergic receptor agonist. In yet other embodiments, the prodrug has a distinct organ-specific distribution as compared to the corresponding $\alpha_{2A}$-adrenergic receptor agonist. Non-limiting examples of kinds of prodrugs contemplated within the invention are recited in the following patent application publications, each of which is incorporated by reference in its entirety herein: US 2012/0065152; WO 2011/033296; and US 2011/0065796.

Methods

The invention includes a method of preventing or reducing risk of cortical degeneration in a mammal in need thereof. The method comprises administering to the mammal a therapeutically effective amount of at least one $\alpha_{2A}$-adrenergic receptor agonist, whereby cortical degeneration is prevented or risk thereof is reduced.

The invention further includes a method of preserving cognition in a mammal in need thereof. The method comprises administering to the mammal a therapeutically effective amount of at least one $\alpha_{2A}$-adrenergic receptor agonist, whereby cognition in the mammal is preserved.

In certain embodiments, the agonist comprises at least one selected from the group consisting of guanfacine; brimonidine; guanabenz; guanoxabenz; a salt or solvate thereof and mixtures thereof.

In certain embodiments, the agonist comprises at least one selected from the group consisting of clonidine; xylazine; dexmedetomidine; detomidine; medetomidine; a salt or solvate thereof and mixtures thereof.

In certain embodiments, the agonist is administered to the mammal as part of a pharmaceutically acceptable composition. In other embodiments, the agonist is administered to the mammal by a route comprising at least one selected from the group consisting of inhalational, oral, rectal, vaginal, parenteral, topical, transdermal, pulmonary, intranasal, buccal, sublingual, ophthalmic, intrathecal, intravenous and intragastrical.

In certain embodiments, the agonist is formulated as part of an extended-release formulation. In other embodiments, the mammal is administered a prodrug of the $\alpha_{2A}$-adrenergic receptor agonist.

In certain embodiments, the daily dose of agonist ranges from about 0.001 mg/kg/day to about 0.1 mg/kg/day. In other embodiments, the daily dose of agonist ranges from about 0.001 mg/kg/day to about 0.01 mg/kg/day. In yet other embodiments, the daily dose of agonist ranges from about 0.01 mg/kg/day to about 0.1 mg/kg/day. In yet other embodiments, the daily dose of agonist is about 0.01 mg/kg/day.

In certain embodiments, the mammal does not present symptoms of a neurodegenerative disease or disorder. In other embodiments, the mammal has not been diagnosed with a neurodegenerative disease or disorder. In yet other embodiments, the mammal presents symptoms of a neurodegenerative disease or disorder. In yet other embodiments, the mammal has been diagnosed with a neurodegenerative disease or disorder. In other embodiments, the neurodegenerative disease or disorder comprises Alzheimer's disease, Parkinson's disease, frontal temporal dementia, a tauopathy, chronic traumatic encephalopathy, traumatic brain injury, and mild cognitive impairment.

In certain embodiments, the mammal does not have a disease or disorder that is a risk factor for the development of dementia or other cognitive disorders. In other embodiments, the mammal has a disease or disorder that is a risk factor for the development of dementia or other cognitive disorders. In yet other embodiments, the mammal has been diagnosed with a disease or disorder that is a risk factor for the development of dementia or other cognitive disorders. In yet other embodiments, the mammal has not been diagnosed with a disease or disorder that is a risk factor for the development of dementia or other cognitive disorders. In yet other embodiments, the disease or disorder comprises at least one selected from the group consisting of Alzheimer's disease, Parkinson's disease, frontal temporal dementia, a tauopathy, chronic traumatic encephalopathy, traumatic brain injury, and mild cognitive impairment.

In certain embodiments, the mammal has a disease or disorder with cognitive symptoms. In other embodiments, the mammal does not have a disease or disorder with cognitive symptoms. In yet other embodiments, the mammal has not been diagnosed with a disease or disorder with cognitive symptoms. In yet other embodiments, the disease or disorder comprises at least one selected from the group consisting of major depressive disorder, anxiety disorders, multiple sclerosis, cancer, chemotherapy side effects, bipolar disorder, schizophrenia, diabetes, Lyme disease, and hypertension.

In certain embodiments, the administration of the agonist inhibits or reverses formation of phosphorylated tau in the prefrontal cortex of the mammal. In other embodiments, the administration of the agonist inhibits or reverses formation of phosphorylated COXIV in the prefrontal cortex of the mammal.

In certain embodiments, the mammal is a primate. In other embodiments, the primate is human.

Combination Therapies

The compounds of the present invention are intended to be useful in the methods of present invention in combination with one or more additional compounds useful for treating the diseases or disorders contemplated within the invention. These additional compounds may comprise compounds of the present invention or compounds, e.g., commercially available compounds, known to treat, prevent, or reduce the symptoms of the diseases or disorders contemplated within the invention.

A synergistic effect may be calculated, for example, using suitable methods such as, for example, the Sigmoid-$E_{max}$ equation (Holford & Scheiner, 19981, Clin. Pharmacokinet. 6: 429-453), the equation of Loewe additivity (Loewe & Muischnek, 1926, Arch. Exp. Pathol Pharmacol. 114: 313-326) and the median-effect equation (Chou & Talalay, 1984, Adv. Enzyme Regul. 22: 27-55). Each equation referred to above may be applied to experimental data to generate a corresponding graph to aid in assessing the effects of the drug combination. The corresponding graphs associated with the equations referred to above are the concentration-effect curve, isobologram curve and combination index curve, respectively.

Administration/Dosage/Formulations

The regimen of administration may affect what constitutes an effective amount. The therapeutic formulations may be administered to the patient either prior to or after the onset of a disease or disorder. Further, several divided dosages, as well as staggered dosages may be administered daily or sequentially, or the dose may be continuously infused, or may be a bolus injection. Further, the dosages of the therapeutic formulations may be proportionally increased or decreased as indicated by the exigencies of the therapeutic or prophylactic situation.

Administration of the compositions useful within the present invention to a patient, preferably a mammal, more preferably a human, may be carried out using known procedures, at dosages and for periods of time effective to treat a disease or disorder in the patient. An effective amount of the therapeutic compound necessary to achieve a therapeutic effect may vary according to factors such as the state of the disease or disorder in the patient; the age, sex, and weight of the patient; and the ability of the therapeutic compound to treat a disease or disorder in the patient. Dosage regimens may be adjusted to provide the optimum therapeutic response. For example, several divided doses may be administered daily or the dose may be proportionally reduced as indicated by the exigencies of the therapeutic situation. A non-limiting example of an effective dose range for a therapeutic compound of the invention is from about 1 and 5,000 mg/kg of body weight/per day. One of ordinary skill in the art would be able to study the relevant factors and make the determination regarding the effective amount of the therapeutic compound without undue experimentation.

Actual dosage levels of the active ingredients in the pharmaceutical compositions of this invention may be varied so as to obtain an amount of the active ingredient that is effective to achieve the desired therapeutic response for a particular patient, composition, and mode of administration, without being toxic to the patient.

In particular, the selected dosage level will depend upon a variety of factors including the activity of the particular compound employed, the time of administration, the rate of excretion of the compound, the duration of the treatment, other drugs, compounds or materials used in combination with the compound, the age, sex, weight, condition, general health and prior medical history of the patient being treated, and like factors well, known in the medical arts.

A medical doctor, e.g., physician or veterinarian, having ordinary skill in the art may readily determine and prescribe the effective amount of the pharmaceutical composition required. For example, the physician or veterinarian could start doses of the compounds of the invention employed in the pharmaceutical composition at levels lower than that required in order to achieve the desired therapeutic effect and gradually increase the dosage until the desired effect is achieved.

In particular embodiments, it is especially advantageous to formulate the compound in dosage unit form for ease of administration and uniformity of dosage. Dosage unit form as used herein refers to physically discrete units suited as unitary dosages for the patients to be treated; each unit containing a predetermined quantity of therapeutic compound calculated to produce the desired therapeutic effect in association with the required pharmaceutical vehicle. The dosage unit forms of the invention are dictated by and directly dependent on (a) the unique characteristics of the therapeutic compound and the particular therapeutic effect to be achieved, and (b) the limitations inherent in the art of compounding/formulating such a therapeutic compound for the treatment of a disease or disorder in a patient.

In certain embodiments, the compositions useful within the invention are formulated using one or more pharmaceutically acceptable excipients or carriers. In certain embodiments, the pharmaceutical compositions of the invention comprise a therapeutically effective amount of a compound useful within the invention and a pharmaceutically acceptable carrier.

The carrier may be a solvent or dispersion medium containing, for example, water, ethanol, polyol (for example, glycerol, propylene glycol, and liquid polyethylene glycol, and the like), suitable mixtures thereof, and vegetable oils. The proper fluidity may be maintained, for example, by the use of a coating such as lecithin, by the maintenance of the required particle size in the case of dispersion and by the use of surfactants. Prevention of the action of microorganisms may be achieved by various antibacterial and antifungal agents, for example, parabens, chlorobutanol, phenol, ascorbic acid, thimerosal, and the like. In many cases, it will be preferable to include isotonic agents, for example, sugars, sodium chloride, or polyalcohols such as mannitol and sorbitol, in the composition. Prolonged absorption of the injectable compositions may be brought about by including in the composition an agent which delays absorption, for example, aluminum monostearate or gelatin.

In certain embodiments, the compositions useful within the invention are administered to the patient in dosages that range from one to five times per day or more. In other embodiments, the compositions useful within the invention are administered to the patient in range of dosages that include, but are not limited to, once every day, every two, days, every three days to once a week, and once every two weeks. It will be readily apparent to one skilled in the art that the frequency of administration of the various combination compositions useful within the invention will vary from individual to individual depending on many factors including, but not limited to, age, disease or disorder to be treated, gender, overall health, and other factors. Thus, the invention should not be construed to be limited to any particular dosage regime and the precise dosage and composition to be administered to any patient will be determined by the attending physical taking all other factors about the patient into account.

Compounds for administration may be in the range of from about 1 µg to about 10,000 mg, about 20 µg to about 9,500 mg, about 40 µg to about 9,000 mg, about 75 µg to about 8,500 mg, about 150 µg to about 7,500 mg, about 200 µg to about 7,000 mg, about 3050 µg to about 6,000 mg, about 500 µg to about 5,000 mg, about 750 µg to about 4,000 mg, about 1 mg to about 3,000 mg, about 10 mg to about 2,500 mg, about 20 mg to about 2,000 mg, about 25 mg to about 1,500 mg, about 50 mg to about 1,000 mg, about 75 mg to about 900 mg, about 100 mg to about 800 mg, about 250 mg to about 750 mg, about 300 mg to about 600 mg, about 400 mg to about 500 mg, and any and all whole or partial increments therebetween.

In certain embodiments, the dose of a compound is from about 1 mg and about 2,500 mg. In other embodiments, a dose of a compound of the invention used in compositions described herein is less than about 10,000 mg, or less than about 8,000 mg, or less than about 6,000 mg, or less than about 5,000 mg, or less than about 3,000 mg, or less than about 2,000 mg, or less than about 1,000 mg, or less than about 500 mg, or less than about 200 mg, or less than about 50 mg. Similarly, in certain embodiments, a dose of a second compound (i.e., a drug used for treating a disease or disorder) as described herein is less than about 1,000 mg, or less than about 800 mg, or less than about 600 mg, or less than about 500 mg, or less than about 400 mg, or less than about 300 mg, or less than about 200 mg, or less than about 100 mg, or less than about 50 mg, or less than about 40 mg, or less than about 30 mg, or less than about 25 mg, or less than about 20 mg, or less than about 15 mg, or less than about 10 mg, or less than about 5 mg, or less than about 2 mg, or less than about 1 mg, or less than about 0.5 mg, and any and all whole or partial increments thereof.

In certain embodiments, the present invention is directed to a packaged pharmaceutical composition comprising a container holding a therapeutically effective amount of a compound of the invention, alone or in combination with a second pharmaceutical agent; and instructions for using the compound to treat, prevent, or reduce one or more symptoms of a disease or disorder in a patient.

Formulations may be employed in admixtures with conventional excipients, i.e., pharmaceutically acceptable organic or inorganic carrier substances suitable for oral, parenteral, nasal, intravenous, subcutaneous, enteral, or any other suitable mode of administration, known to the art. The pharmaceutical preparations may be sterilized and if desired mixed with auxiliary agents, e.g., lubricants, preservatives, stabilizers, wetting agents, emulsifiers, salts for influencing osmotic pressure buffers, coloring, flavoring and/or aromatic substances and the like. They may also be combined where desired with other active agents, e.g., other cognition improving agents.

The term "container" includes any receptacle for holding the pharmaceutical composition. For example, In certain embodiments, the container is the packaging that contains the pharmaceutical composition. In other embodiments, the container is not the packaging that contains the pharmaceutical composition, i.e., the container is a receptacle, such as a box or vial that contains the packaged pharmaceutical composition or unpackaged pharmaceutical composition and the instructions for use of the pharmaceutical composition. Moreover, packaging techniques are well known in the art. It should be understood that the instructions for use of the pharmaceutical composition may be contained on the packaging containing the pharmaceutical composition, and as such the instructions form an increased functional relationship to the packaged product. However, it should be understood that the instructions may contain information pertaining to the compound's ability to perform its intended function, e.g., treating, preventing, or reducing a disease or disorder in a patient.

Routes of administration of any of the compositions of the invention include oral, nasal, rectal, intravaginal, parenteral, buccal, sublingual or topical. The compounds for use in the invention may be formulated for administration by any suitable route, such as for oral or parenteral, for example, transdermal, transmucosal (e.g., sublingual, lingual, (trans) buccal, (trans)urethral, vaginal (e.g., trans- and perivaginally), (intra)nasal and (trans)rectal), intravesical, intrapulmonary, intraduodenal, intragastrical, intrathecal, subcutaneous, intramuscular, intradermal, intra-arterial, intravenous, intrabronchial, inhalation, and topical administration.

Suitable compositions and dosage forms include, for example, tablets, capsules, caplets, pills, gel caps, troches, dispersions, suspensions, solutions, syrups, granules, beads, transdermal patches, gels, powders, pellets, magmas, lozenges, creams, pastes, plasters, lotions, discs, suppositories, liquid sprays for nasal or oral administration, dry powder or aerosolized formulations for inhalation, compositions and formulations for intravesical administration and the like. It should be understood that the formulations and compositions that would be useful in the present invention are not limited to the particular formulations and compositions that are described herein.

Non-limiting examples of formulations useful within the invention, including formulations of prodrugs of compounds useful within the invention, are recited in the following patent application publications, each of which is incorporated by reference in its entirety herein: US 2012/0065152; WO 2011/033296; US 2011/0065796; and WO 2007/016284.

Oral Administration

For oral application, particularly suitable are tablets, dragees, liquids, drops, suppositories, or capsules, caplets and gelcaps. The compositions intended for oral use may be prepared according to any method known in the art and such compositions may contain one or more agents selected from the group consisting of inert, non-toxic pharmaceutically excipients which are suitable for the manufacture of tablets. Such excipients include, for example an inert diluent such as lactose; granulating and disintegrating agents such as cornstarch; binding agents such as starch; and lubricating agents such as magnesium stearate. The tablets may be uncoated or they may be coated by known techniques for elegance or to delay the release of the active ingredients. Formulations for oral use may also be presented as hard gelatin capsules wherein the active ingredient is mixed with an inert diluent.

For oral administration, the compounds may be in the form of tablets or capsules prepared by conventional means with pharmaceutically acceptable excipients such as binding agents (e.g., polyvinylpyrrolidone, hydroxypropylcellulose or hydroxypropylmethylcellulose); fillers (e.g., cornstarch, lactose, microcrystalline cellulose or calcium phosphate); lubricants (e.g., magnesium stearate, talc, or silica); disintegrates (e.g., sodium starch glycollate); or wetting agents (e.g., sodium lauryl sulphate). If desired, the tablets may be coated using suitable methods and coating materials such as OPADRY™ film coating systems available from Colorcon, West Point, Pa. (e.g., OPADRY™ OY Type, OYC Type, Organic Enteric OY-P Type, Aqueous Enteric OY-A Type, OY-PM Type and OPADRY™ White, 32K18400). Liquid preparation for oral administration may be in the form of solutions, syrups or suspensions. The liquid preparations may be prepared by conventional means with pharmaceutically acceptable additives such as suspending agents (e.g., sorbitol syrup, methyl cellulose or hydrogenated edible fats); emulsifying agent (e.g., lecithin or acacia); non-aqueous vehicles (e.g., almond oil, oily esters or ethyl alcohol); and preservatives (e.g., methyl or propyl p-hydroxy benzoates or sorbic acid).

Granulating techniques are well known in the pharmaceutical art for modifying starting powders or other particulate materials of an active ingredient. The powders are typically mixed with a binder material into larger permanent free-flowing agglomerates or granules referred to as a "granulation." For example, solvent-using "wet" granulation processes are generally characterized in that the powders are combined with a binder material and moistened with water or an organic solvent under conditions resulting in the formation of a wet granulated mass from which the solvent must then be evaporated.

Melt granulation generally consists in the use of materials that are solid or semi-solid at room temperature (i.e. having a relatively low softening or melting point range) to promote granulation of powdered or other materials, essentially in the absence of added water or other liquid solvents. The low melting solids, when heated to a temperature in the melting point range, liquefy to act as a binder or granulating medium. The liquefied solid spreads itself over the surface of powdered materials with which it is contacted, and on cooling, forms a solid granulated mass in which the initial materials are bound together. The resulting melt granulation may then be provided to a tablet press or be encapsulated for preparing the oral dosage form. Melt granulation improves the dissolution rate and bioavailability of an active (i.e. drug) by forming a solid dispersion or solid solution.

U.S. Pat. No. 5,169,645 discloses directly compressible wax-containing granules having improved flow properties. The granules are obtained when waxes are admixed in the melt with certain flow improving additives, followed by cooling and granulation of the admixture. In certain embodiments, only the wax itself melts in the melt combination of the wax(es) and additives(s), and in other cases both the wax(es) and the additives(s) will melt.

The present invention also includes a multi-layer tablet comprising a layer providing for the delayed release of one or more compounds of the invention, and a further layer providing for the immediate release of a medication for treatment of a disease or disorder. Using a wax/pH-sensitive polymer mix, a gastric insoluble composition may be obtained in which the active ingredient is entrapped, ensuring its delayed release.

Parenteral Administration

For parenteral administration, the compounds may be formulated for injection or infusion, for example, intravenous, intramuscular or subcutaneous injection or infusion, or for administration in a bolus dose and/or continuous infusion. Suspensions, solutions or emulsions in an oily or aqueous vehicle, optionally containing other formulatory agents such as suspending, stabilizing and/or dispersing agents may be used.

Additional Administration Forms

Additional dosage forms of this invention include dosage forms as described in U.S. Pat. Nos. 6,340,475, 6,488,962, 6,451,808, 5,972,389, 5,582,837, and 5,007,790. Additional dosage forms of this invention also include dosage forms as described in U.S. Patent Applications Nos. 20030147952, 20030104062, 20030104053, 20030044466, 20030039688, and 20020051820. Additional dosage forms of this invention also include dosage forms as described in PCT Applications Nos. WO 03/35041, WO 03/35040, WO 03/35029, WO 03/35177, WO 03/35039, WO 02/96404, WO 02/32416, WO 01/97783, WO 01/56544, WO 01/32217, WO 98/55107, WO 98/11879, WO 97/47285, WO 93/18755, and WO 90/11757.

Controlled Release Formulations and Drug Delivery Systems

In certain embodiments, the formulations of the present invention may be, but are not limited to, short-term, rapid-offset, as well as controlled, for example, sustained release, delayed release and pulsatile release formulations.

The term sustained release is used in its conventional sense to refer to a drug formulation that provides for gradual release of a drug over an extended period of time, and that may, although not necessarily, result in substantially constant blood levels of a drug over an extended time period. The period of time may be as long as a month or more and should be a release which is longer that the same amount of agent administered in bolus form.

For sustained release, the compounds may be formulated with a suitable polymer or hydrophobic material which provides sustained release properties to the compounds. As such, the compounds for use the method of the invention may be administered in the form of microparticles, for example, by injection or in the form of wafers or discs by implantation.

In a preferred embodiment of the invention, the compounds of the invention are administered to a patient, alone or in combination with another pharmaceutical agent, using a sustained release formulation.

The term delayed release is used herein in its conventional sense to refer to a drug formulation that provides for an initial release of the drug after some delay following drug administration and that mat, although not necessarily, includes a delay of from about 10 minutes up to about 12 hours.

The term pulsatile release is used herein in its conventional sense to refer to a drug formulation that provides release of the drug in such a way as to produce pulsed plasma profiles of the drug after drug administration.

The term immediate release is used in its conventional sense to refer to a drug formulation that provides for release of the drug immediately after drug administration.

As used herein, short-term refers to any period of time up to and including about 8 hours, about 7 hours, about 6 hours, about 5 hours, about 4 hours, about 3 hours, about 2 hours, about 1 hour, about 40 minutes, about 20 minutes, or about 10 minutes and any or all whole or partial increments thereof after drug administration after drug administration.

As used herein, rapid-offset refers to any period of time up to and including about 8 hours, about 7 hours, about 6 hours, about 5 hours, about 4 hours, about 3 hours, about 2 hours, about 1 hour, about 40 minutes, about 20 minutes, or about 10 minutes, and any and all whole or partial increments thereof after drug administration.

Dosing

The therapeutically effective amount or dose of a compound will depend on the age, sex and weight of the patient, the current medical condition of the patient and the progression of cognitive changes in the patient being treated. The skilled artisan will be able to determine appropriate dosages depending on these and other factors.

A suitable dose of a compound of the present invention may be in the range of from about 0.01 mg to about 5,000 mg per day, such as from about 0.1 mg to about 1,000 mg, for example, from about 1 mg to about 500 mg, such as about 5 mg to about 250 mg per day. The dose may be administered in a single dosage or in multiple dosages, for example from 1 to 4 or more times per day. When multiple dosages are used, the amount of each dosage may be the same or different. For example, a dose of 1 mg per day may be administered as two 0.5 mg doses, with about a 12-hour interval between doses.

It is understood that the amount of compound dosed per day may be administered, in non-limiting examples, every day, every other day, every 2 days, every 3 days, every 4 days, or every 5 days. For example, with every other day administration, a 5 mg per day dose may be initiated on Monday with a first subsequent 5 mg per day dose administered on Wednesday, a second subsequent 5 mg per day dose administered on Friday, and so on.

The compounds for use in the method of the invention may be formulated in unit dosage form. The term "unit dosage form" refers to physically discrete units suitable as unitary dosage for patients undergoing treatment, with each unit containing a predetermined quantity of active material calculated to produce the desired therapeutic effect, optionally in association with a suitable pharmaceutical carrier. The unit dosage form may be for a single daily dose or one of multiple daily doses (e.g., about 1 to 4 or more times per day). When multiple daily doses are used, the unit dosage form may be the same or different for each dose.

Those skilled in the art will recognize, or be able to ascertain using no more than routine experimentation, numerous equivalents to the specific procedures, embodiments, claims, and examples described herein. Such equivalents were considered to be within the scope of this invention and covered by the claims appended hereto. For example, it should be understood, that modifications in reaction conditions, including but not limited to reaction times, reaction size/volume, and experimental reagents, such as solvents, catalysts, pressures, atmospheric conditions, e.g., nitrogen atmosphere, and reducing/oxidizing agents, with art-recognized alternatives and using no more than routine experimentation, are within the scope of the present application.

It is to be understood that wherever values and ranges are provided herein, all values and ranges encompassed by these values and ranges, are meant to be encompassed within the scope of the present invention. Moreover, all values that fall within these ranges, as well as the upper or lower limits of a range of values, are also contemplated by the present application.

The following examples further illustrate aspects of the present invention. However, they are in no way a limitation of the teachings or disclosure of the present invention as set forth herein.

EXAMPLES

The invention is now described with reference to the following Examples. These Examples are provided for the purpose of illustration only, and the invention is not limited to these Examples, but rather encompasses all variations that are evident as a result of the teachings provided herein.

Methods & Materials

Tissue Preparation for Immunoelectron Microscopy:

Three young adults (9, 10, 11-year old) and six aged (24, 25, 26, 29, 31, 33-year old) rhesus macaques were used for the anatomical studies. The animals were perfused transcardially with artificial cerebrospinal fluid, followed by 4% paraformaldehyde/0.05% glutaraldehyde, plus 15% aqueous saturated picric acid in 0.1 M phosphate buffer (PB). The brains were blocked coronally, vibrosliced at 60 µm, cryoprotected and stored at −80° C. Sections of the dlPFC went through three freeze-thaw cycles in liquid nitrogen to facilitate penetration of immunoreagents, and processed for single and dual immunocytochemistry.

PDE4A or pSer214-Tau, AT8 or PHF Single Immunocytochemistry:

Sections were incubated for 36 h in rabbit anti-PDE4A IgG (Abcam, ab14607; 1:300) or mouse anti-CP3 IgM (Jicha et al., 1999, J Neurosci. 19:7486) (1:100), ptau pSer202+Thr205 antibody (AT8), or PHF antibodies, followed by species-specific biotinylated antibodies and the avidin-biotinylated peroxidase reaction using DAB as a chromogen. Alternatively, secondary antibodies were conjugated to 1.4 nm gold cluster and visualized with silver intensification of gold (FIGS. 3A-3B). The procedures and immunoprobes are described in detail in Paspalas et al., 2013, Cereb. Cortex 23:1643.

PDE4A-AKAP6 Double Immunocytochemistry:

Sections were incubated for 48 h in a mixture of anti-PDE4A and mouse anti-AKAP6 IgG (Sigma-Aldrich, SAB1401476; 1:200). Biotin- or 1.4 nm gold-conjugated species-specific secondary antibodies were used to label PDE4A with DAB, as described for single immunocytochemistry, and AKAP6 with silver intensification of gold (Paspalas et al., 2013, Cereb. Cortex 23:1643).

Electron Microscopy and Data Analysis:

Labeled tissue was processed for electron microscopy using 40 nm-thick plastic sections, and omitting counterstaining to facilitate detection of the weakest signal. Quantitative analyses were performed on series of low magnification micrographs, each covering a field of 462 µm. A comprehensive account of tissue sampling and data collection is published in Paspalas et al., 2013, Cereb. Cortex 23:1643.

Heat-Stable Tau Preparations from Frozen Rhesus Macaque Cortical Tissue:

Heat-stable tau was prepared as detailed in Bussière et al., 2003, J Comp Neurol. 463:281. Small blocks of dlPFC were surgically removed and flash-frozen before perfusion of subjects. A piece was placed into ice-cold homogenization buffer (10 mM Tris pH 7.4, 140 mM NaCl, 2 mM EGTA, plus protease and phosphatase inhibitors; 400 µL per 100 mg tissue) and homogenized by sonication. A small fraction was reserved for protein quantification for gel loading. NaCl was added to 250 mM, followed by addition of β-mercaptoethanol (14.3 M, Sigma) to 5% total volume. Samples were vortexed and heated to 100° C. for 15 min, vortexed, then cooled on ice for 30 min. Lysates were cleared by centrifugation at 16,100×g for 10 min at 4° C., and the supernatant used for immunoblotting. Band intensities were normalized by total heat-stable protein, quantified by measurement of major band intensities on a Coomassie stained gel (FIG. 5C).

Immunoblots:

All samples were run on Invitrogen Novex 4-12% Tris-glycine gels using the Biorad Western blotting system. Lanes were transferred onto 0.2 µM Nitrocellulose (Biorad) and incubated overnight in primary antibodies: anti PDE4A (Abcam, ab14607; 1:1000), anti-GAPDH (Advanced Immunochemical, mAb 6C5; 1:5000), anti-PDE4B (Pearson et al., 1985, Proc. Natl. Acad. Sci. USA 82:4531), anti-β-tubulin (T2200, Sigma; 1:5000), anti-PSD95 (EMD Millipore, mAb N68; 1:5000), anti-pSer214 (EMD Millipore, AB6972; 1:1000) for all experiments, except the primary culture experiment, where Abcam 4846 was used due to discontinuation of the previous antibody, anti-pThr231 (Pierce, OPA1-031556; 1:1000), anti-tau (clone 5E2, EMD Millipore, 05-348; 1:500-1:1000). Primary antibodies were labeled using the appropriate Licor IRDye 680 or 800 secondary antibody, and visualized using a Licor Odyssey Infra Red Scanner. Bands were quantified using Odyssey Software, and statistics performed by Student's T-test, unless stated otherwise.

Electrophysiological Recordings:

The effects of the PDE4 inhibitor, etazolate, on the persistent firing of dlPFC Delay cells were examined in two young adult male (9 and 10-year old) and one aged female (21-year old) rhesus macaques. Recording in aged monkeys requires patience, as these animals are more fragile and perform fewer trials than younger adults (Lewis et al., 1987, J Neurosci. 7:1799).

All monkeys had been previously trained on the ODR task (FIG. 10). Eye position was monitored with the ISCAN Eye Movement Monitoring System (ISCAN, Burlington, Mass.), and the ODR task was generated by the TEMPO real-time system (Reflective Computing, St. Louis, Mo.). Prior to recording, the animals underwent MRI scans to obtain the exact anatomical coordinates of brain structures, which guided placement of the chronic recording chambers. MRI-compatible materials were used for the implant so that another MRI could be performed after implantation to confirm the position of the recording chambers. Delay-related cells were obtained from the dlPFC ranging from −1-3 3 mm anterior to the caudal end of the principal sulcus and −1-2 mm medial to the principal sulcus (FIG. 10).

Once stable neuronal recordings were established, iontophoretic experiments began. Iontophoretic electrodes were constructed with a 20 µm-pitch carbon fiber (ELSI, San Diego, Calif.) inserted in the central barrel of a seven-barrel non-filamented capillary glass (Friedrich and Dimmock, Millville, N.J.). The assembly was pulled using a custom electrode puller (PMP-107, Microdata Instrument Inc., South Plainfield, N.J.) and the tip was beveled to obtain the finished electrode. Finished electrodes had impedances of 0.3-1.0 MΩ (at 1 kHz) and tip sizes of 30-40 µm. The outer barrels of the electrode were filled with three drug solutions (two consecutive barrels each), and the solutions were pushed to the tip of the electrode using compressed air. Delivery of the drugs was controlled with Neurophore BH2 iontophoretic system (Medical Systems Corp., Greenvale, N.Y.). Etazolate (Tocris Bioscience, Minneapolis Minn.) was ejected at 5, 10 or 25 nA. Retaining currents of −5 to −10 nA were used in a cycled manner (1 sec on, 1 sec off) when not applying drugs. Drug ejection did not create noise in the recording, and there was no systematic change in either spike amplitude or time course at any ejection current. The electrode was mounted on a MO-95 micromanipulator (Narishige, East Meadow, N.Y.) in a 25-gauge stainless steel guide tube. The dura was punctured using the guide tube to facilitate access of the electrode to cortex. Extracellular voltage was amplified using a custom low-noise preamplifier (SKYLAB) and band-pass filtered (180 Hz-6 Khz, 20 dB gain, 4-pole Butterworth; Kron-Hite, Avon, Mass.). Signals were digitized (15 kHz, micro 1401, Cambridge Electronics Design, Cambridge, UK) and acquired using the Spike2 software (CED, Cambridge, UK). Neural activity was analyzed using waveform sorting by a template-matching algorithm, which made it possible to isolate more than one unit at the same recording site. Post-stimulus time histograms (PSTHs) and rastergrams were constructed online to determine the relationship of unit activity to the task. Unit activity was measured in spikes per second. If the rastergrams displayed delay-related activity, the units were recorded further and pharmacological testing was performed.

Data were first collected from the cell under control condition where at least 8 trials at each of 8 cue locations were obtained. Upon establishing the stability of the cells' activity, this control condition (0 nA) was followed by iontophoretic application of etazolate. Iontophoresis allows application of minute amounts of drug next to the neuron without fluid currents that move the neuron and disrupt recordings. Given the extremely small amounts of drug applied, only a few neurons are affected, not altering cognitive performance. Etazolate was continuously applied at a relevant current (5, 10 or 25 nA) throughout a given condition. Each condition had ~8 (6-12) trials at each location for statistical analyses of effects. A total of 39 delay-related cells were recorded and tested with drug. Data were analyzed by ANOVA.

Post-Synaptic Density Preparations:

Mice were killed by rapid decapitation, and the frontal cortex rapidly dissected into 1 ml of homogenization buffer (20 mM HEPES pH 7.4, 0.32 M sucrose, protease and phosphatase inhibitors). Two cortical sections were pooled to provide approximately 100 mg of tissue. The pooled sample was immediately homogenized using a Glas-col Variable Speed Homogenizer set to 40%, and 10 vertical strokes of the pestle on ice. The sample was then centrifuged at 1000×g for 1 min at 4° C. to remove debris. The supernatant was transferred to a new tube and further centrifuged at 2000×g for 10 min at 4° C. to remove nuclei (P1). The supernatant was then transferred to a new tube and centrifuged at 15,000×g for 10 min at 4° C., resulting in the supernatant, denoted S2, and the synaptoneurosome fraction in the pellet. The pellet was resuspended in 300 µl of homogenization buffer and applied to the top of a Percoll Gradient consisting of homogenization buffer with 23%, 15%, 10% and 3% of Percoll, respectively. The gradient was ultracentrifuged at 25,000×g for 12 min at 4° C. The interface between the 15 and 23% layers was collected as the "pure" (p4) synaptoneurosome fraction, and pooled with the interface between the 10% and 15% fraction, collected as the "crude" (p3) synaptoneurosome fraction (there is some contamination with membranes). The pellets were then resuspended in 3 volumes of Lysis Buffer (20 mM HEPES pH 7.4, 1 mM DTT, protease and phosphatase inhibitors) and incubated for 30 min on ice, resulting in hypotonic lysis of synaptoneurosomes. The sample was then centrifuged at 25,000×g for 30 min at 4° C. The supernatant was removed (the spinoplasm) and the pellet resuspended in 2 ml of Triton Buffer (20 mM HEPES pH 7.4, 0.32 M sucrose, 0.75% Triton X-100) to extract the Triton insoluble PSD. Samples were incubated on ice for 15 min, then centrifuged at 63,000×g for 30 min at 4° C. The supernatant was removed (the membrane) and the pellet washed in 1 ml PBS. Finally, the sample was centrifuged at 63,000×g for 30 min at 4° C., the PBS removed, and the pellet resuspended in PBS with 1% SDS, quantified by BCA assay (Thermo Scientific) and used for immunoblotting.

cAMP Measurement:

cAMP levels in the medial PFC of young adult (6 months, n=7) vs. aged (24 months, n=4) Brown Norway rats were assayed. Rats were sacrificed by focused microwave radiation in proportion to body weight (5.0 to 6.5 kW, 1.4 sec duration), decapitated and brains rapidly removed and frozen. The medial PFC was dissected from the frozen brains, and immediately sonicated in microcentrifuge tubes containing 0.5 ml of 0.1 M HCl/0.5% Triton X-100 on ice. Samples were cleared by centrifugation, and supernatants used for cAMP assays using the Correlate-EIA Enzyme Immunoassay Kit (Assay Designs Inc). All samples and standards were run in duplicate, and results were averaged. cAMP concentrations were determined by reference to a standard curve using nonlinear regression in SYSTAT and estimates (in pmol cAMP) were divided by the tissue mass. Data were analyzed by one-way ANOVA.

Primary Cortical Neuron Culture:

Primary cortical neurons were prepared from P1 C57Bl/6 mice. One day prior to neuron production, plates were coated overnight with Poly-D-Lysine solution (Sigma). P1 mouse brains were removed in ice cold dissection buffer (HBSS, L-glutamine, 7 mM HEPES, all GIBCO). Cortices were microdissected, and the hippocampi discarded. Tissue was then transferred to 0.1% trypsin solution, and incubated for 45 min before 5 passages through a wide plastic Pasteur pipette. The remaining tissue was triturated to a single cell suspension, and the resulting solution passed through a 40 µM cell filter (Biorad). Cells were plated at a density of $5 \times 10^5$ live cells per well (6 well plates) in Neurobasal media plus B27 supplement, Glutamax and Pen/Strep solution. Cells were incubated at 37° C., 5% $CO_2$, with media replenished every 7 days.

pSer214 Phosphorylation assays in Cultured Neurons

Assays were performed on primary cortical neurons between 7-11 days in vitro. Cells were preincubated with vehicle or 10 µM rolipram in DMSO (Sigma) for 10 min. After preincubation, cells were treated with increasing concentrations of forskolin (Abcam; 100, 200, 500, 1000 nM in DMSO) in the presence or absence of 10 µM rolipram for a further 10 min. Cells were lysed in PBS containing 1% SDS, plus protease and phosphatase inhibitors, and heated to 70° C. immediately for 10 min to ensure inactivation of phosphatases. Samples were quantified by BCA assay, and analyzed by immunoblotting. In this instance, band intensity was quantified using ImageJ, and significance assessed by 2 way ANOVA using Graph Pad Prism software.

Example 1

Figure 1A:
FIGS. 1A-1D illustrate the finding that phosphorylated tau increases with age in monkey dlPFC.
Figure 1B:
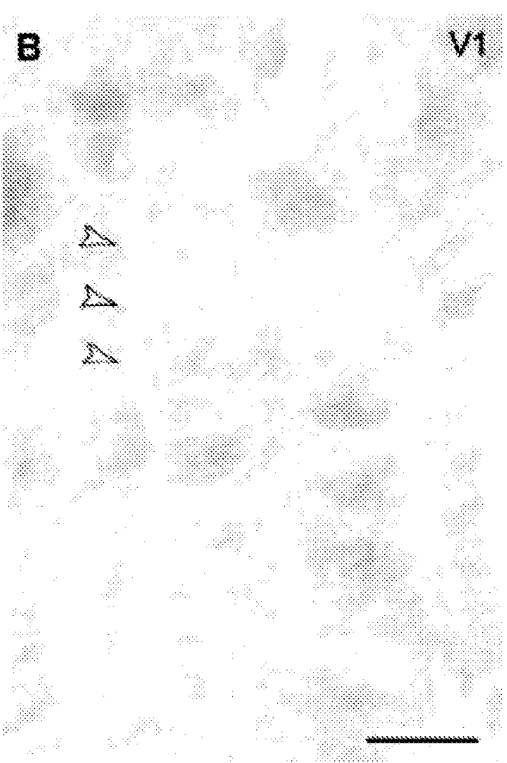
Figure 1C:
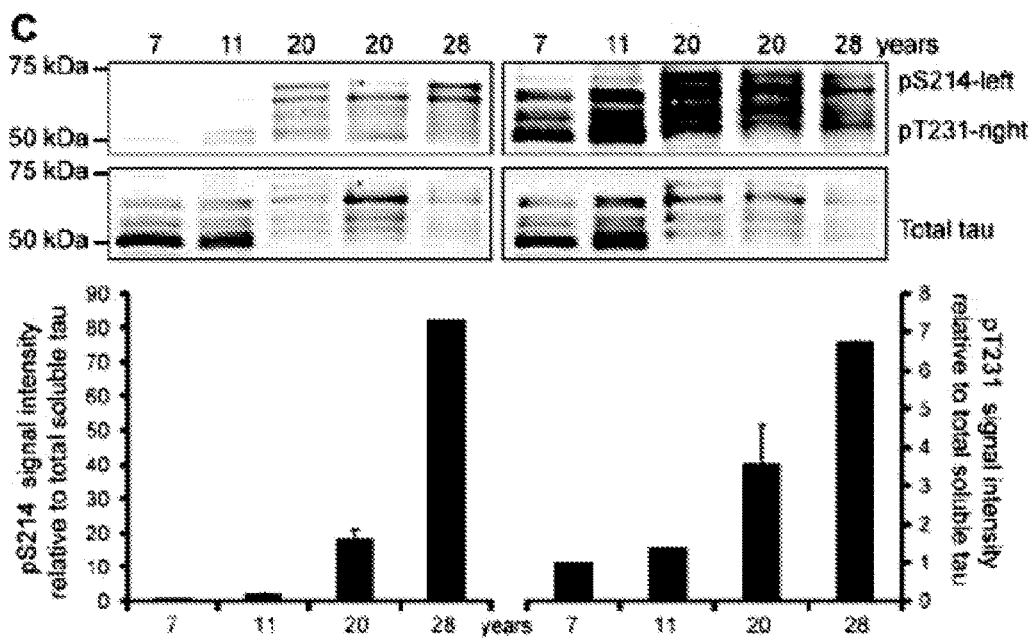
Figure 5A:
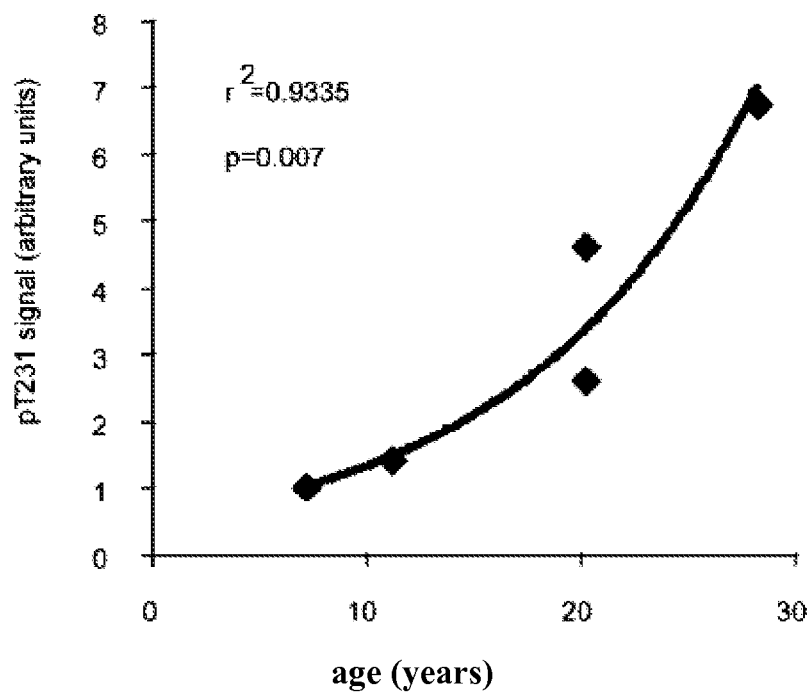
FIGS. 5A-5C illustrate the finding that p-Tau increases with age in monkey dlPFC.
Figure 5B:
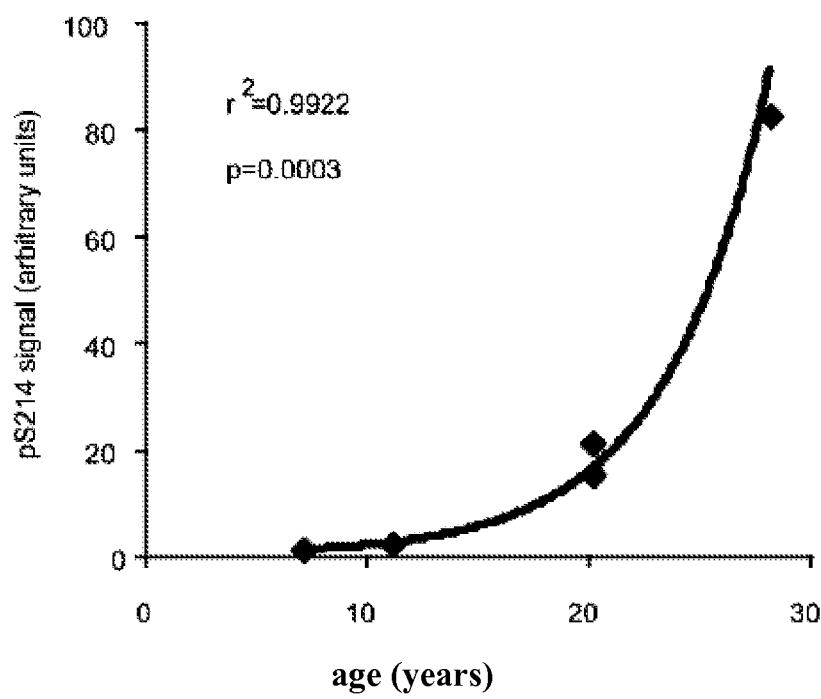
Figure 5C:
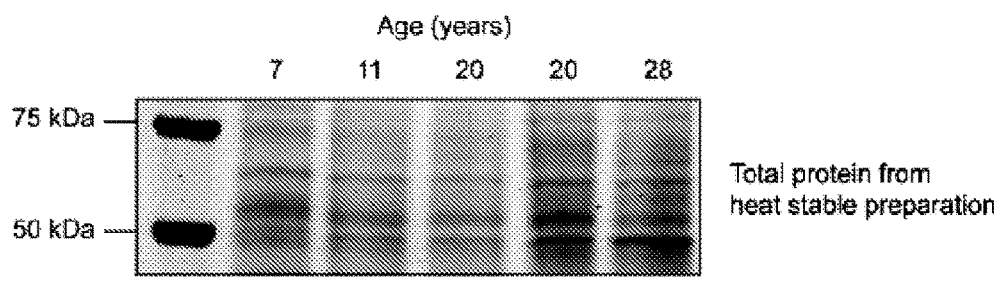
Figure 6:
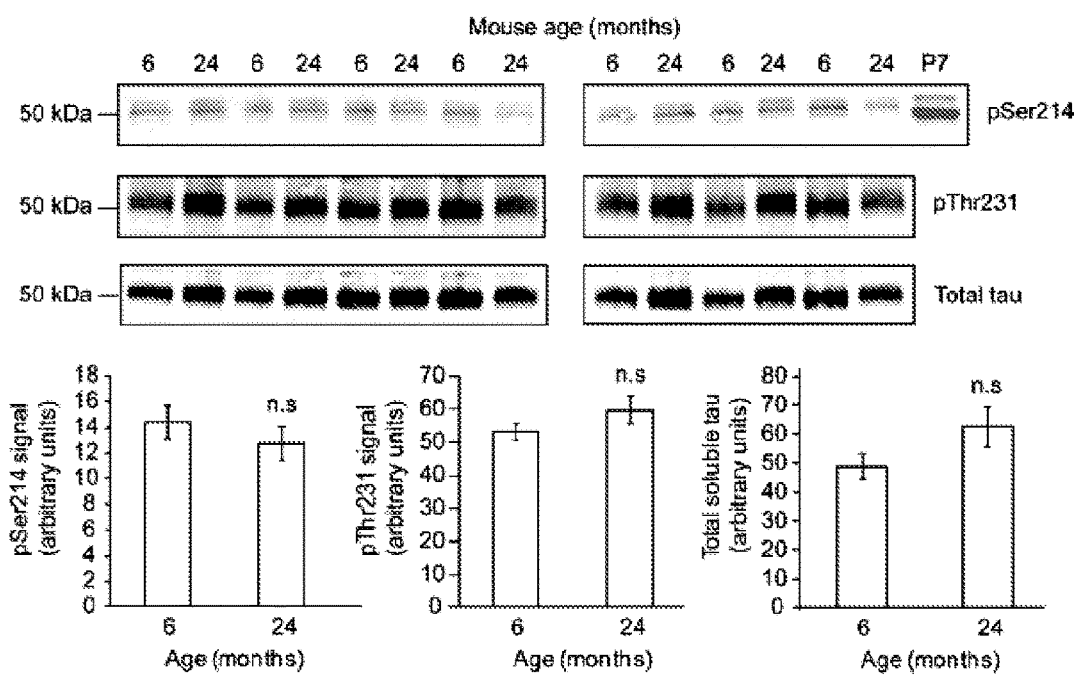
FIG. 6 illustrates the finding that Tau is not highly phosphorylated at Ser214 in adult mouse frontal cortex Immunoblots of heat-stable protein extracts from mouse whole frontal cortex. Blots were labeled for pSer214 (Millipore, AB9672), pThr231 (Thermo, PA1-14418) and total Tau (Millipore, 05-348, clone 5E2). Quantification showed no significant differences with age for either phosphorylation site or total soluble tau obtained from the preparations. The final lane on the pSer214 blot showed P7 total mouse brain as a positive control given low signals in adult mouse brain. Error bars on graphs show standard error of the mean.

Immunocytochemistry against pS214-tau in aged monkey revealed extensive reactivity of layer III pyramidal cells in dlPFC (FIG. 1A), but not in V1 (FIG. 1B), similar to the pattern of NFT in AD Immunoblotting of heat-stable preparations demonstrated a highly significant correlation of pS214-tau expression in monkey dlPFC with increasing age ($r^2=0.9922$, p=0.0003), as well as age-related reductions in soluble tau, consistent with increasing fibrillation (FIGS. 1C and 5). Age-related increases in tau phosphorylation were also observed at threonine 231 (pT231; $r^2=0.9335$, p=0.007; FIG. 1C), a site that is phosphorylated by a number of kinases, e.g. CaM kinase II, GSK-3 and cdk5 (Sengupta et al., 1998, Arch. Biochem. Biophys. 357:299). In contrast to the aging monkey, there were only background levels of pS214-tau and no significant change with age in pT231-tau in mouse medial PFC (FIG. 6), emphasizing that normal mice are not appropriate for modeling AD. Moreover, the aging monkey can help reveal vulnerabilities in higher cortical circuits with ultrastructural clarity not possible in human post-mortem tissue.

Figure 1D:
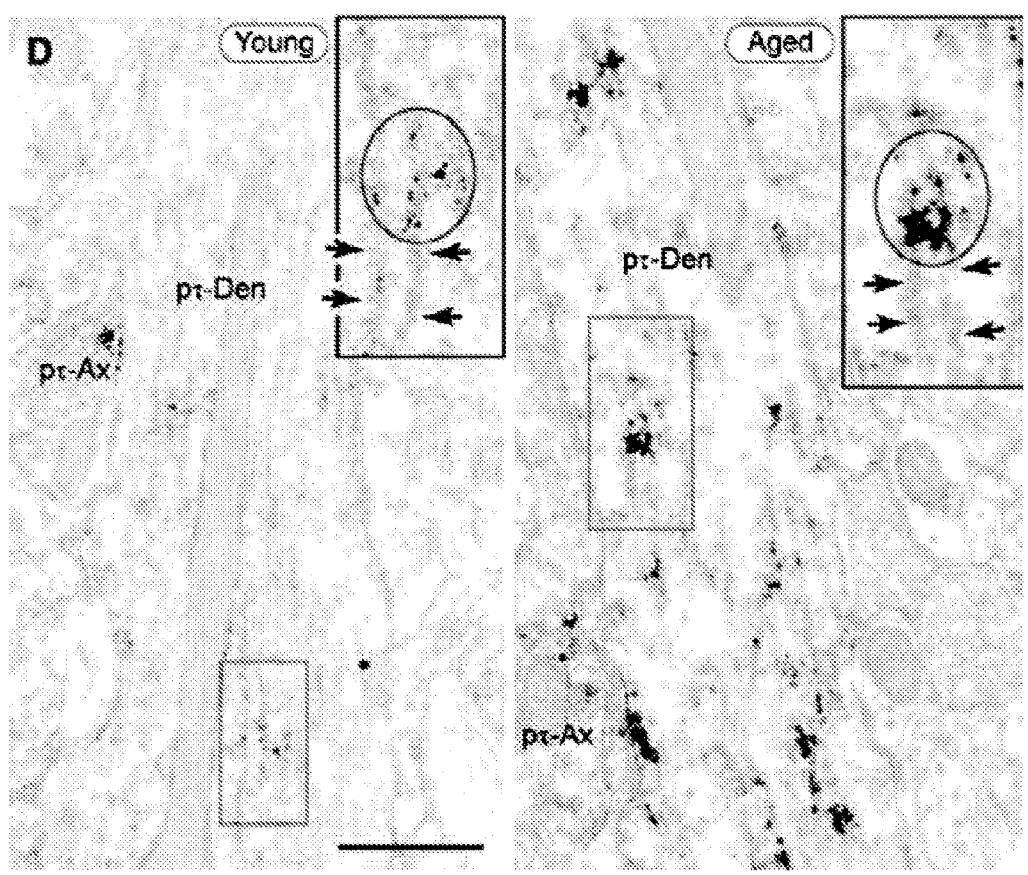
Figure 7A:
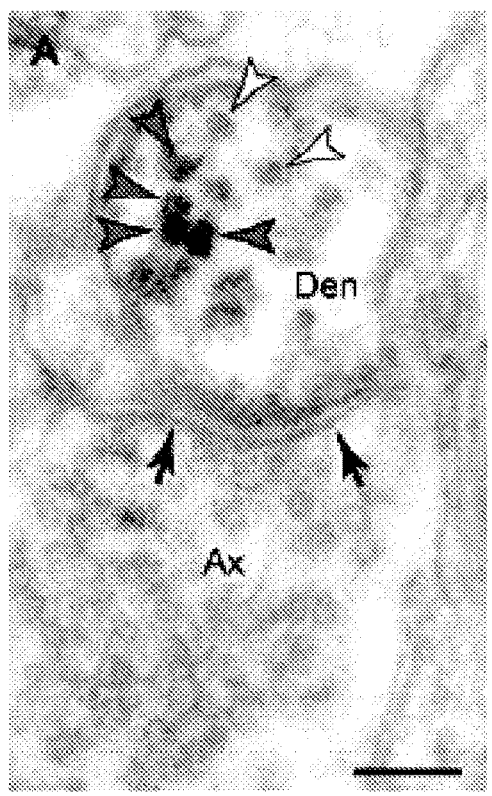
FIGS. 7A-7B are a set of images illustrating the subcellular expression of p-tau in the neuropil of aged monkey dlPFC: dendritic shaft.
Figure 7B:
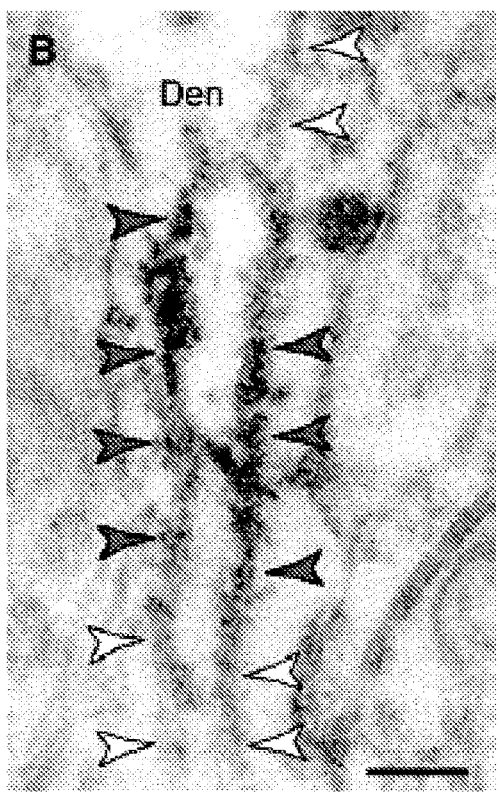
Figure 8A:
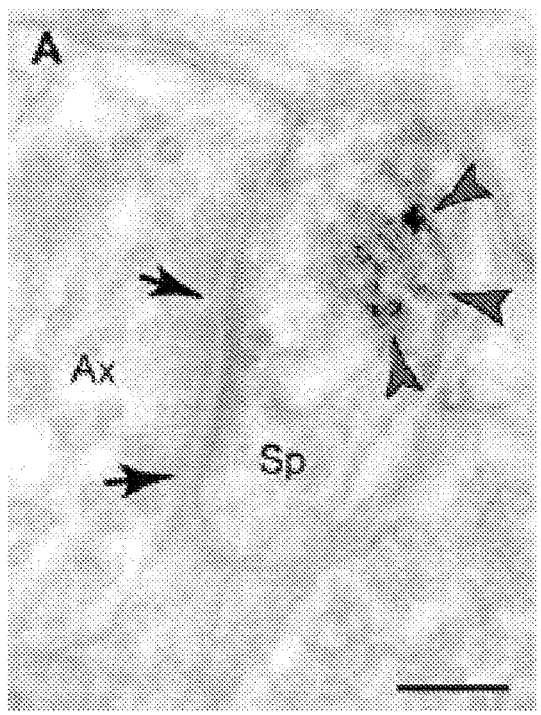
FIGS. 8A-8B are a set of images illustrating the subcellular expression of p-tau in the neuropil of aged monkey dlPFC: dendritic spine.
Figure 8B:
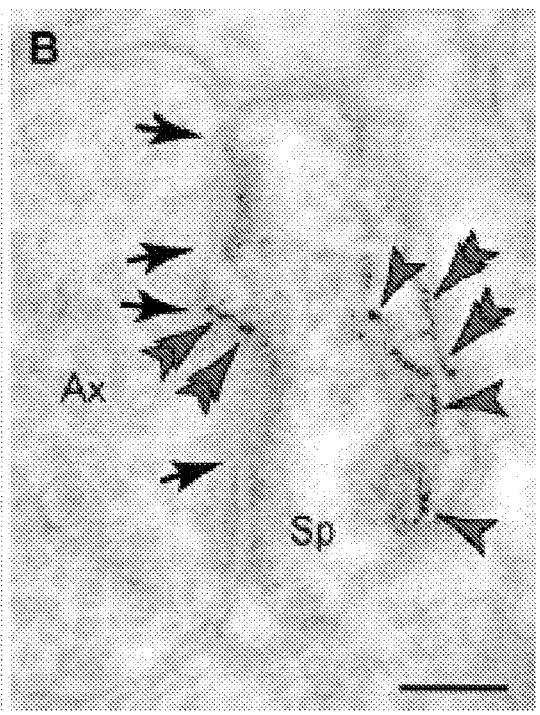
Figure 9A:
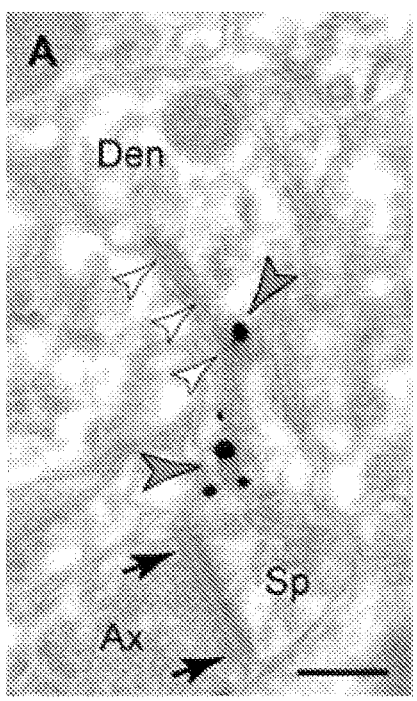
FIGS. 9A-9D are a series of images illustrating AKAP6 localization and colocalization with PDE4A in young monkey dlPFC. PKA was tethered by anchoring proteins, including AKAP6. These images documented AKAP6 on the SA (pseudocolored), which stores and releases $Ca^{2+}$, similar to the SER. Inositol trisphosphate receptor (IP3R) stimulation initiates internal $Ca^{2+}$ release through ryanodine receptors (RyRs), and IP3Rs are found on the SA in primate dlPFC. cAMP-PKA signaling increases internal $Ca^{2+}$ release by increasing the efficacy and expression of IP3R, and by increasing $Ca^{2+}$ leak through RyRs. Increased $Ca^{2+}$ release may in turn promote cAMP production, fueling feedforward signaling.
Figure 9B:
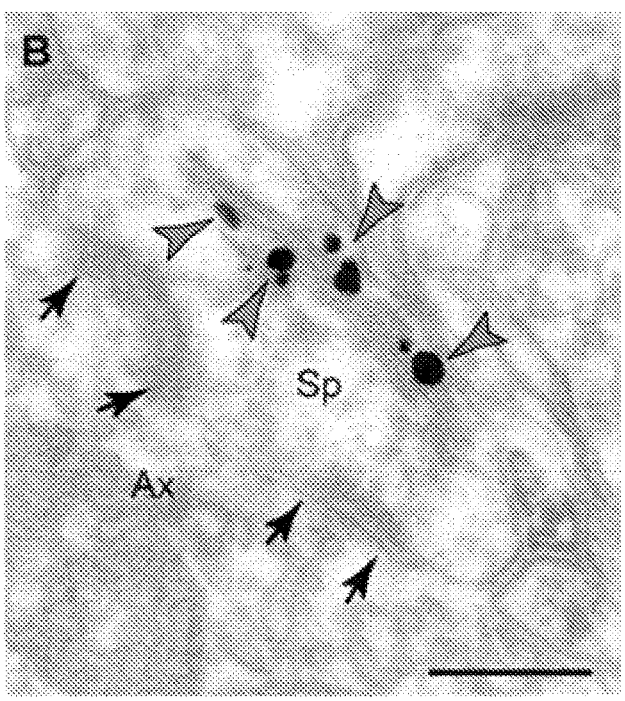
Figure 9C:
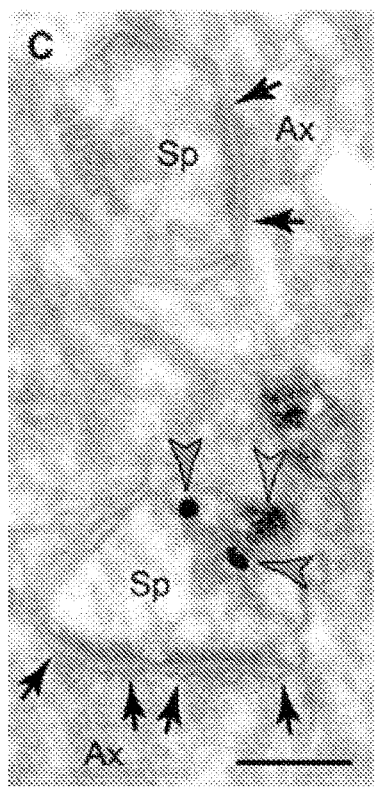
Figure 9D:
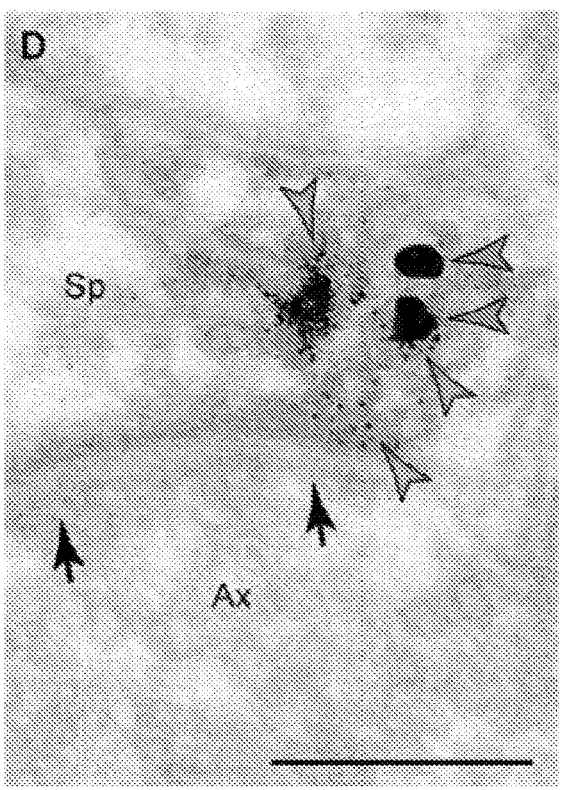
Figure 10A:
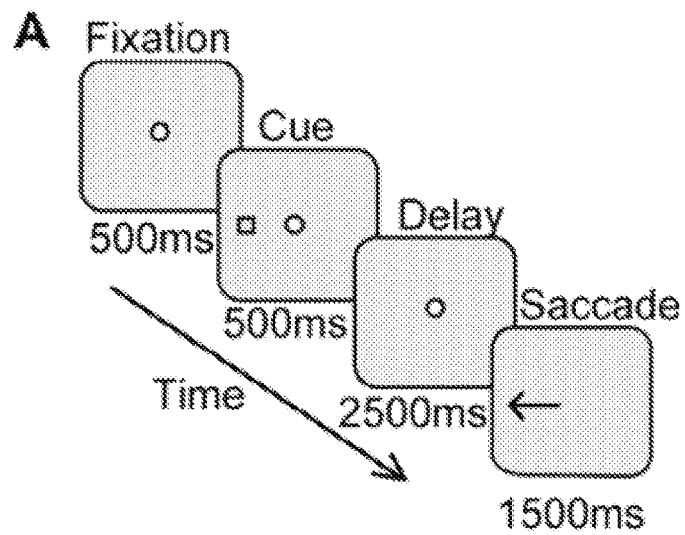
Figure 10B:
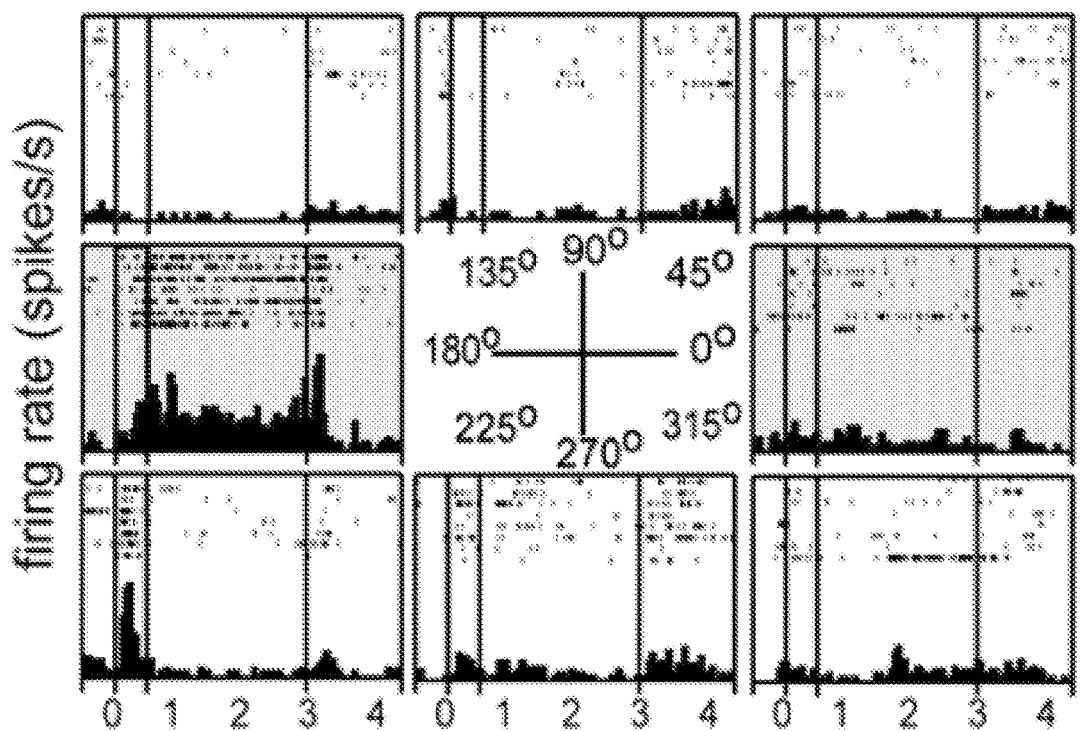
Figure 10C:
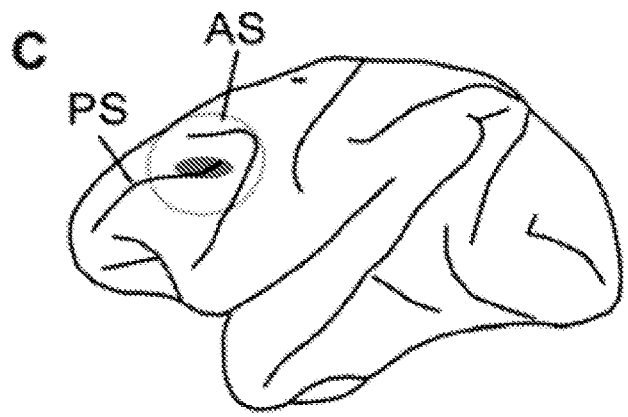
Figure 10D:
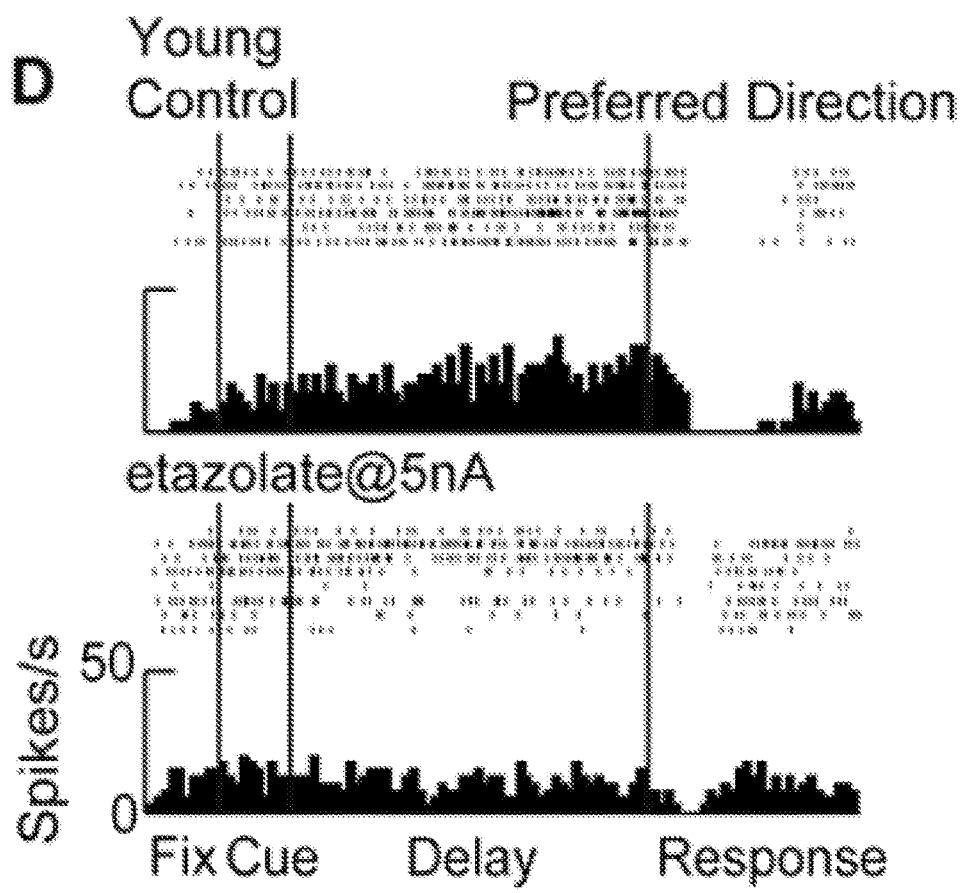

Immunoelectron microscopy (immunoEM) of pS214-tau was performed in young (9-11 yrs) vs. aged (24-31 yrs) monkey dlPFC to determine its subcellular distribution in layer III pyramidal cells. In young dlPFC (FIG. 1D), p-tau prevailed in axons and certain proximal dendrites, with fine labeling along the microtubules (pS214-tau-profiles: 68% axons, 8% dendrites, 4% spines, 20% non-identified). This contrasted with aged dlPFC, where pS214-tau was heavily aggregated in dendrites over microtubule bundles (FIGS. 1D and 7) and in spines (pS214-tau-profiles: 23% axons, 18% dendrites, 43% spines, 16% non-identified). In aged spines, pS214-tau accumulated at the post-synaptic density (PSD; FIGS. 2A-2B), and the spine apparatus (SA), the specialized extension of smooth endoplasmic reticulum (SER) that segregates internal $Ca^{2+}$ in spines (FIGS. 2C and 8). Importantly, pS214-tau was selective to spine glutamatergic synapses, and was lacking in symmetric, inhibitory synapses on spines (FIG. 2B), or synapses on dendrites (FIG. 7A). Thus, pS214-tau aggregates directly over aging NMDA receptor synapses where pyramidal cell circuits interconnect (schematically summarized in FIG. 4).

The superb monkey ultrastructure allowed the first "snapshots" of p-tau trafficking in the brain, i.e., a distinct association with endoplasmic vesicles and exo/endocytotic membrane profiles. In the young dlPFC, vesicular pS214-tau profiles of 50 nm appeared exclusively in axons, and particularly at axo-axonal appositions where they observed fusing with the axolemma to form omega-shaped profiles (FIG. 2D). In the aged dlPFC, pS214-tau vesicular profiles were no longer encountered in axons, but found instead in dendritic spines, either at asynaptic membranes at axon appositions or directly within the synapse per se (FIG. 2E). Taken together, these data suggest trans-axonal spreading of pS214-tau in young dlPFC, while in the aged dlPFC, pS214-tau-reactive vesicles may capture trafficking within the spine (e.g., towards the glutamatergic synapse; FIG. 2E) or possibly trans-neuronal transport. The superb monkey ultrastructure also allowed the first evidence of NFT formation in the entorhinal association cortex of an extremely old (33 yo) rhesus monkey (FIGS. 20A-20B), as evidenced by classic, paired helical filaments (PHFs) comprised of hyperphosphorylated tau, which are the building blocks of NFTs in AD. The periodicity of the helix was the same as that found in human AD.

Figure 3E:
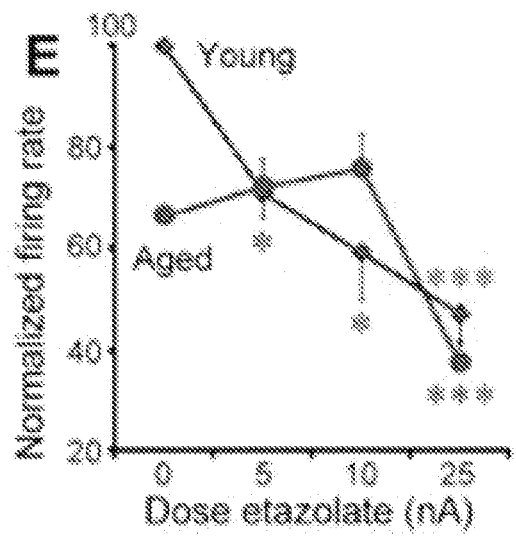
Figure 3F:
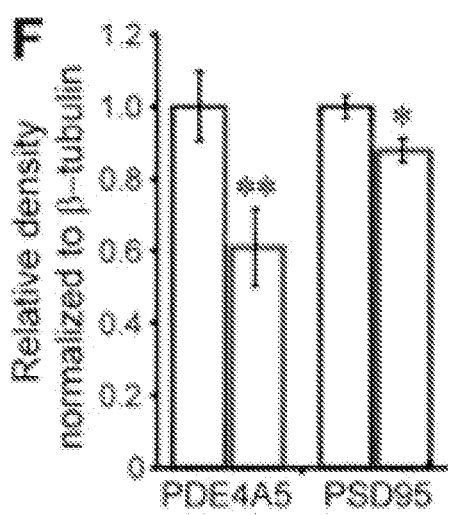
Figure 3G:
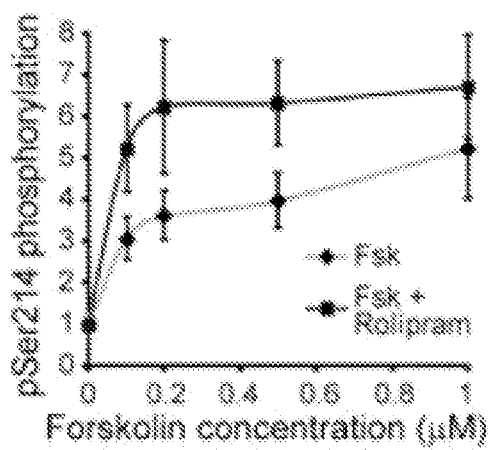
Figure 11A:
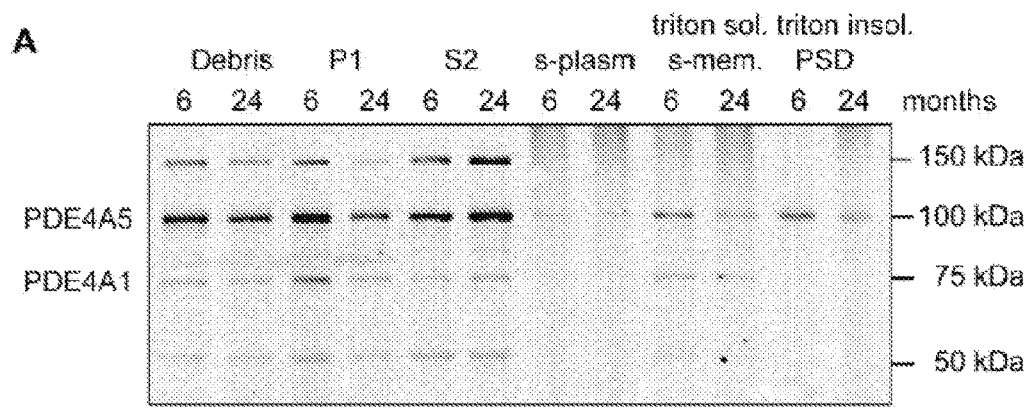
FIGS. 11A-11C are a series of immunoblots and bar graphs illustrating the distribution of PDE4s through the mouse PSD preparation.
Figure 11B:
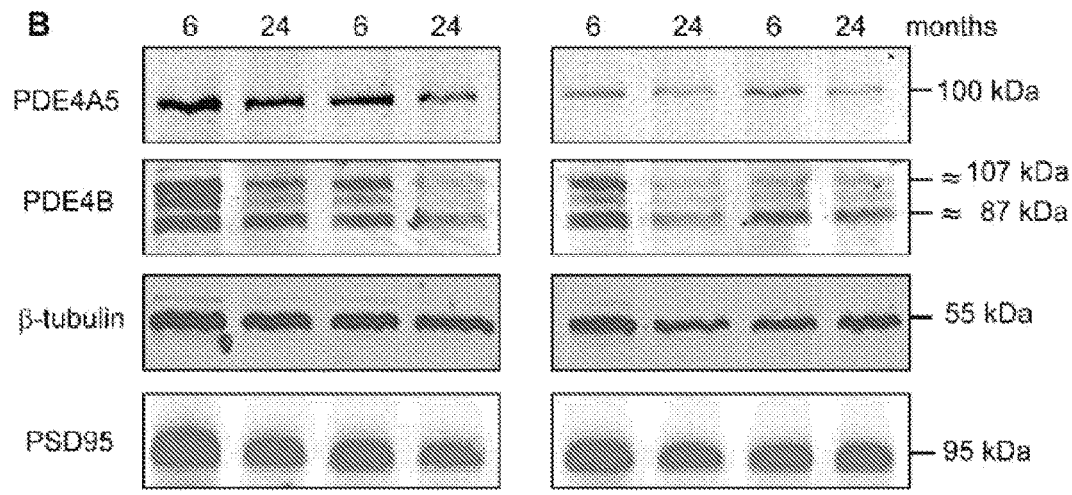
Figure 11C:
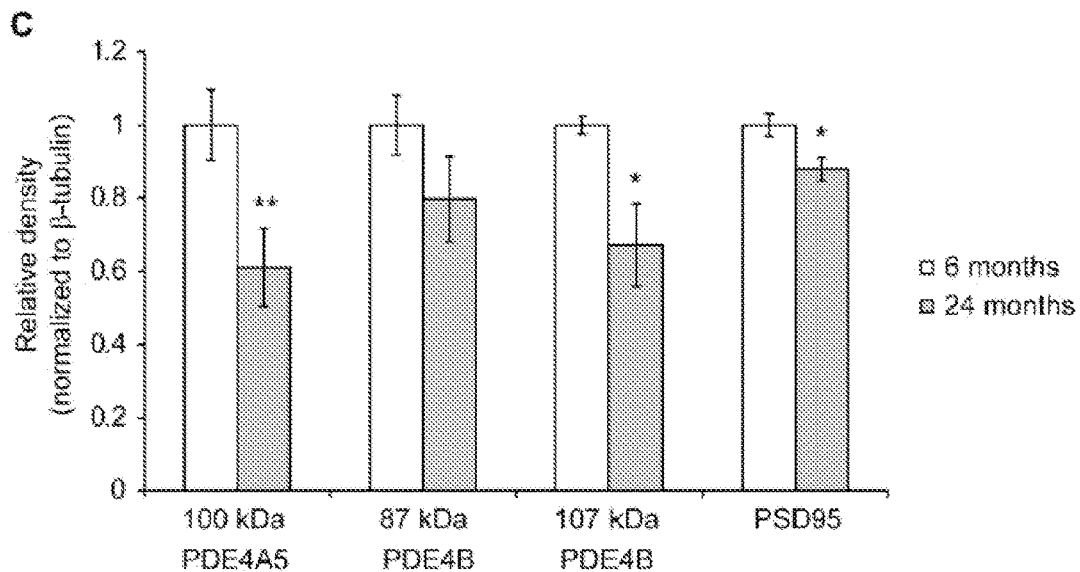
Figure 12:
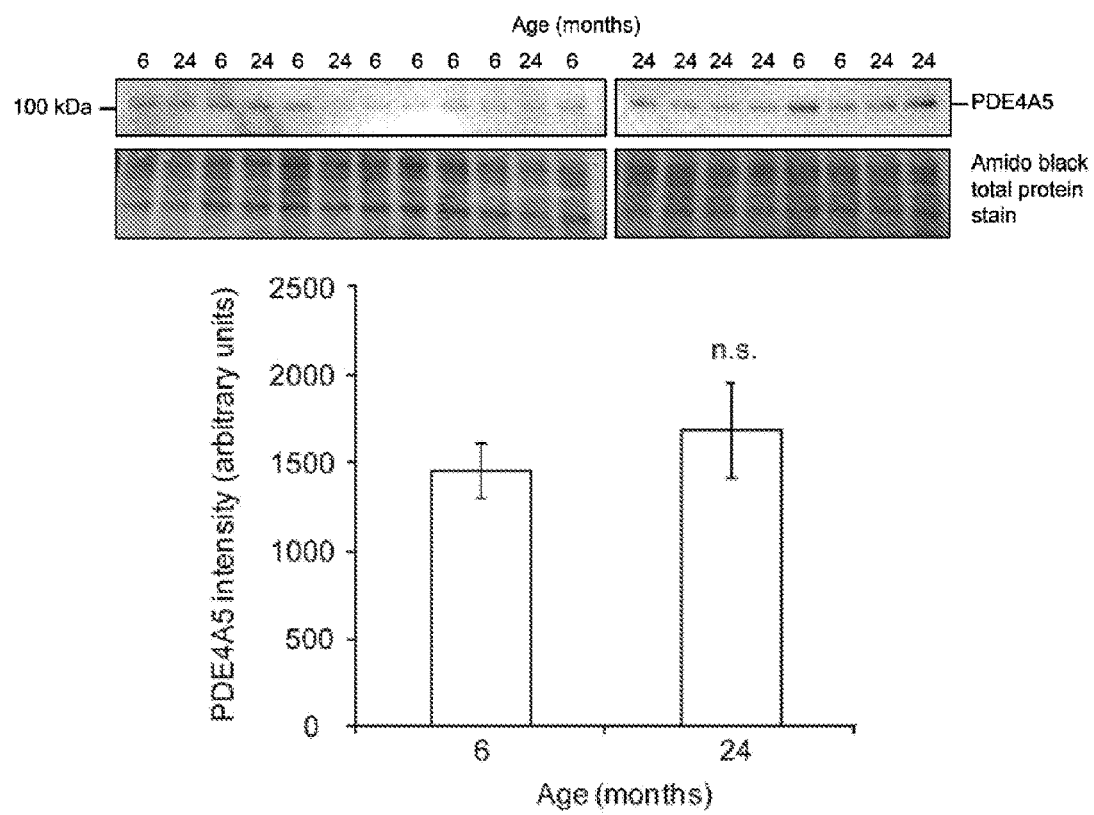
FIG. 12 illustrates PDE4A5 in total lysate from mouse PFC Immunoblot labeled for PDE4A (Abcam, ab14607) in 6 month-old vs. 24 month-old total tissue lysate from a punch of flash frozen PFC. The signal-to-noise ratio was low, reflecting the fact that PDE4A5 was difficult to discern in total lysate from mouse brain. PDE4A5 band intensity was normalized by Amido black total protein stain (Sigma), and the quantification is shown in the graph. No significant effect of age on PDE4A5 expression was detected.
Figure 13:
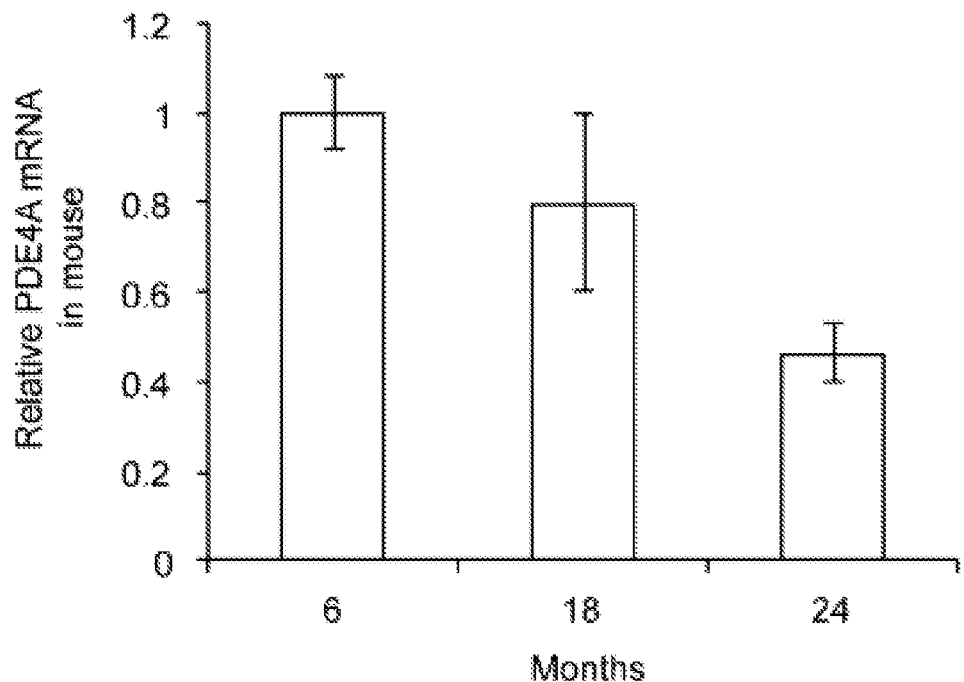
FIG. 13 is a bar graph illustrating the finding that qPCR using a pan PDE4A probe showed a significant decrease in PDE4A mRNA with age in flash-frozen mouse PFC. Monotonic decrease in expression was found to be significant by one way ANOVA; $p<0.02$ ($F(2,18)=5.185$). Error bars represent the standard error. Samples normalized using probes for the reference genes TBP and RSP, which were found to be stable with increasing age. Forward pan PDE4A probe.

Comparisons of the young vs. aged monkey dlPFC indicate that increasing PKA phosphorylation of tau may involve age-related loss of the phosphodiesterase PDE4A from spines. In young dlPFC, PDE4A is prevalent in layer III spines, localized near the SA (FIGS. 3A-3B) along with the PKA tethering A-kinase anchor protein 6 (AKAP6, FIG. 9), where it is positioned to regulate feedforward cAMP-$Ca^{2+}$ signaling. In young dlPFC, cAMP-$Ca^{2+}$ signaling opens $K^+$ channels on spines to modulate network connectivity and enhance mental flexibility (schematically illustrated in FIG. 4). $Ca^{2+}$ signaling is dysregulated in aging brain, and increases in cAMP-PKA signaling in aged PFC are associated with reduced neuronal firing and impaired cognition. However, it has not been known why cAMP-PKA become dysregulated with age. The present study found loss of PDE4A from aged spines, mirroring the location where pS214-tau accumulates in the aged dlPFC. Quantitative immunoEM showed a selective loss of PDE4A from spines in aged monkey dlPFC, although it remained in glia and dendrites (FIG. 3C; 10 yrs: PDE4A-spines/46 $\mu m^2$=5.95 (+2.13 SD), i.e., 39.5% (+14.9% SD) of total spines; 25 yrs: PDE4A-spines/46 $\mu m^2$=2.05 (+1.24 SD), i.e. 16.3% (+8.6% SD) of total spines; n=20). EM data were upheld by quantitative protein assays demonstrating significant decreases in the PDE4A subtype equivalent to mouse PDE4A5 in aged monkey dlPFC (FIG. 3D). The protein data were consistent with physiological recordings from young vs. aged monkeys, where aged dlPFC neurons showed a blunted response to PDE4 inhibition (FIGS. 3E and 10). Similar but much subtler effects were observed in mouse medial PFC, with an age-related reduction in PDE4A5 protein from synapses (FIGS. 3F and 11), which, however, was not evident in whole tissue lysates (FIG. 12). The great expansion in the number of corticocortical synapses in primate dlPFC likely allowed the detection of age-related loss of PDE4A5 in whole tissue. Analysis of rodent PFC also showed reduced PDE4A mRNA with advancing age (FIG. 13), and increased cAMP levels in aged tissue (FIG. 14). Similar disinhibition of cAMP signaling in aged primate spines may increase PKA tau phosphorylation. Inhibition of PDE4 lead to increased PKA phosphorylation of pS214-tau in vitro (FIGS. 3G and 15), suggesting that loss of PDE4A in aged dlPFC spines could similarly lead to pS214-tau accumulation in vivo.

In one aspect, the present study revealed age-related increase in p-tau and reduction in PDE4A in pyramidal cell network synapses in primate association cortex (FIG. 4). The vast expansion of such connections on dendritic spines in primate evolution may magnify this process in human cortex and lead to sufficient phosphorylation to cause fibrillation, NFT formation and neuronal degeneration. The discovery of p-tau aggregation at the spine post-synaptic membrane in aged primate dlPFC suggests that p-tau may interfere with synaptic transmission and receptor trafficking in pyramidal cell networks as part of the normal aging process, which may be exacerbated in those with tau mutations. In addition, the discovery of p-tau in trafficking vesicles provides a possible mechanism for trans-neuronal spread, which has never before been captured in normal, aging brain. Because p-tau aggregates only in asymmetric axospinous synapses in the aged dlPFC, it further illuminates how degeneration could specifically target highly evolved glutamate pyramidal cell circuits with extensive connections on spines. As cAMP-$Ca^{2+}$ signaling is increased in PFC following psychological distress or traumatic brain injury, these data also may help to explain how exposure to psychological or physical trauma exacerbates the degenerative process. The loss of PDE4A from the SA may also aggravate p-tau accumulation in distal dendrites, as large increases in $Ca^{2+}$ release from the SA can spread to SER of the parent dendrite. Increased p-tau, especially in thin, highly branched dendrites, may cause steric hindrance that interferes with intracellular transport, including interference with APP trafficking that can increase production of Aβ. As Aβ oligomers drive intracellular $Ca^{2+}$ release, a vicious cycle could propel the degenerative process. Tau phosphorylation in humans begins relatively early in the aging process, suggesting that interventions need to be initiated at younger ages. The current study demonstrates that the aging monkey can serve as an important animal model for understanding the molecular events that render the association cortices especially vulnerable to degeneration, and an opportunity to test agents that may slow or prevent this process by compensating for PDE4A dysregulation of cAMP signaling in dendritic spines.

Example 2

Vulnerability to degeneration may also involve dysregulation of mitochondrial function, including increased accumulation of ROS. Excessive $Ca^{2+}$ disrupts mitochondrial function, and increased cAMP-PKA activity with advancing age may also contribute to mitochondrial dysfunction. PKA phosphorylates COXIV (p-COXIV), which reduces ATP feedback and increases ROS production. The present data show that p-COXIV increases with advancing age in both primate and mouse prefrontal cortex. Thus, reducing cAMP-PKA signaling may reduce the production of harmful ROS both by decreasing the phosphorylation of COXIV, and by reducing PKA-induced increases in internal $Ca^{2+}$ release. An increase in phosphorylation of COXIV with advancing age was observed in monkey dlPFC, and an increase in signs of ROS was observed in mouse PFC, consistent with mitochondrial dysfunction with advancing age (FIG. 16). Taken together, the present studies show that dysregulated cAMP-PKA signaling with advancing age is associated with increased phosphorylation of COX.

Example 3

At the time of the invention it was not known whether $\alpha_{2A}$ adrenoreceptor (AR) stimulation inhibits phosphorylation of tau or mitochondrial enzymes in aged primates. As demonstrated herein, daily treatment with cognitive-enhancing doses of the $\alpha_{2A}$ adrenoreceptor agonist, guanfacine, reduces the expression of p-tau and phospho-COXIV-1 in the aging association cortex. This indicates that this class of compounds may be used as a preventive treatment for aging humans. Our data suggest that six months of daily treatment with guanfacine (0.001-0.01 mg/kg) enhances cognitive performance (FIG. 17B). The highest dose produced improvement in some monkeys but not in others, likely due to side effects at the higher doses.

Further, a pilot study showed that daily guanfacine treatment produced a dose-related reduction in phosphorylated tau at the pS214 site (FIG. 18) as well as decreasing phospho-COXIV-1 (FIG. 19) in the PFC of aged monkeys (n=1). As $\alpha_{2A}$ agonists such as guanfacine have already been proven safe for long-term treatment in humans, this strategy would be appropriate for long-term, preventative treatment.

Taken together, these data indicate that chronic treatment with $\alpha_{2A}$-AR agonists reduces abnormal phosphorylation in the aged monkey dlPFC, and thus protects the aged primate association cortex from vulnerability for degeneration.

The disclosures of each and every patent, patent application, and publication cited herein are hereby incorporated herein by reference in their entirety.

While the invention has been disclosed with reference to specific embodiments, it is apparent that other embodiments and variations of this invention may be devised by others skilled in the art without departing from the true spirit and scope of the invention. The appended claims are intended to be construed to include all such embodiments and equivalent variations.

What is claimed is:

1. A method of (i) preventing or reducing risk of cortical degeneration in a mammal in need thereof, or (ii) inhibiting or reversing formation of phosphorylated tau or phosphorylated cytochrome oxidase subunit IV (COXIV) in the prefrontal cortex of a mammal in need thereof, the method comprising administering to the mammal a therapeutically effective amount of an $\alpha_{2A}$-adrenergic receptor agonist, wherein the daily dose of the agonist ranges from about 0.001 mg/kg/day to about 0.1 mg/kg/day.

2. The method of claim 1, wherein the agonist comprises at least one selected from the group consisting of guanfacine, brimonidine, guanabenz, guanoxabenz, a salt or solvate thereof, and any mixtures thereof.

3. The method of claim 1, wherein the agonist comprises at least one selected from the group consisting of clonidine, xylazine, dexmedetomidine, detomidine, medetomidine, a salt or solvate thereof, and any mixtures thereof.

4. The method of claim 1, wherein the agonist is administered to the mammal as part of a pharmaceutically acceptable composition.

5. The method of claim 1, wherein the mammal has a disease or disorder that affects or modulates cAMP-$Ca^{2+}$ release in the mammal.

6. The method of claim 1, wherein the mammal does not have symptoms of a neurodegenerative disease or disorder.

7. The method of claim 6, wherein the neurodegenerative disease or disorder comprises at least one selected from the group consisting of Alzheimer's disease, Parkinson's disease, frontal temporal dementia, a tauopathy, chronic traumatic encephalopathy, traumatic brain injury, and mild cognitive impairment.

8. The method of claim 1, wherein the mammal has a disease or disorder that is a risk factor for the development of dementia or other cognitive disorders.

9. The method of claim 8, wherein the disease or disorder comprises at least one selected from the group consisting of major depressive disorder, anxiety disorders, multiple sclerosis, cancer, chemotherapy side effects, bipolar disorder, schizophrenia, diabetes, Lyme disease, and hypertension.

10. The method of claim 1, wherein the agonist is formulated as part of an extended-release formulation.

11. The method of claim 1, wherein the agonist is administered as a prodrug to the mammal.

12. The method of claim 1, wherein the daily dose of agonist is about 0.01 mg/kg/day.

13. The method of claim 1, wherein the mammal is a primate.

14. The method of claim 13, wherein the primate is human.

15. The method of claim 1, wherein the agonist is administered to the mammal by at least one route selected from the group consisting of inhalational, oral, rectal, vaginal, parenteral, topical, transdermal, pulmonary, intranasal, buccal, sublingual, ophthalmic, intrathecal, intravenous and intragastrical.

* * * * *

```
SEQUENCE LISTING

<160> NUMBER OF SEQ ID NOS: 2

<210> SEQ ID NO 1
<211> LENGTH: 20
<212> TYPE: DNA
<213> ORGANISM: Artificial Sequence
<220> FEATURE:
<223> OTHER INFORMATION: chemically synthesized

<400> SEQUENCE: 1
accacaacag cctgcacgca                                                  20

<210> SEQ ID NO 2
<211> LENGTH: 22
<212> TYPE: DNA
<213> ORGANISM: Artificial Sequence
<220> FEATURE:
<223> OTHER INFORMATION: chemically synthesized

<400> SEQUENCE: 2
tgccagctcc gaattggtgt tg                                               22
```